(12) United States Patent
Haghgooie et al.

(10) Patent No.: US 9,119,578 B2
(45) Date of Patent: Sep. 1, 2015

(54) PLASMA OR SERUM PRODUCTION AND REMOVAL OF FLUIDS UNDER REDUCED PRESSURE

(75) Inventors: Ramin Haghgooie, Arlington, MA (US); Donald E. Chickering, III, Framingham, MA (US); Shawn Davis, Boston, MA (US); Mark Michelman, Reading, MA (US); Howard Bernstein, Cambridge, MA (US); Kristin Horton, Brighton, MA (US)

(73) Assignee: Seventh Sense Biosystems, Inc., Cambridge, MA (US)

( * ) Notice: Subject to any disclaimer, the term of this patent is extended or adjusted under 35 U.S.C. 154(b) by 0 days.

(21) Appl. No.: 13/456,505

(22) Filed: Apr. 26, 2012

(65) Prior Publication Data

US 2012/0275955 A1 Nov. 1, 2012

Related U.S. Application Data

(60) Provisional application No. 61/480,941, filed on Apr. 29, 2011, provisional application No. 61/549,437, filed on Oct. 20, 2011.

(51) Int. Cl.
*A61B 5/00* (2006.01)
*A61B 5/15* (2006.01)
(Continued)

(52) U.S. Cl.
CPC ............. *A61B 5/1411* (2013.01); *A61B 5/1438* (2013.01); *A61B 5/14514* (2013.01);
(Continued)

(58) Field of Classification Search
CPC ............. A61B 5/1411; A61B 5/14546; A61B 5/150022; A61B 5/150099; A61B 5/150412; A61B 5/150984; A61B 5/150969; A61B 5/151; A61M 37/0015; B01D 61/145
USPC .................... 422/44; 604/6.01–6.09
See application file for complete search history.

(56) References Cited

U.S. PATENT DOCUMENTS 3,060,429 A 10/1962 Winston
3,072,122 A 1/1963 Rosenthall
(Continued)

FOREIGN PATENT DOCUMENTS

CN 1222334 7/1999
CN 1499949 5/2004
(Continued)

OTHER PUBLICATIONS

European Office Action mailed Jan. 8, 2013 for Application No. 09759467.5.
(Continued)

*Primary Examiner* — Philip R Wiest
*Assistant Examiner* — Benjamin Klein
(74) *Attorney, Agent, or Firm* — Wolf, Greenfield & Sacks, P.C.

(57) ABSTRACT

In some embodiments, the present invention generally relates to the separation of blood within a device to form plasma or serum. In some embodiments, the present invention generally relates to the removal of fluids, such as blood, contained within a device. For example, a device may be applied to the skin of a subject to receive blood from the subject and pass the blood through a separation membrane, which separates the blood into plasma and a portion concentrated in blood cells. As another example, blood or plasma may be allowed to clot within the device and serum (the unclotted portion of the blood) may be withdrawn from the device. The device may contain, in some cases, a vacuum source such as a pre-packaged vacuum to facilitate receiving of blood and/or passage of the blood through the separation membrane to produce plasma or serum.

16 Claims, 8 Drawing Sheets

(51) Int. Cl.
*A61B 5/145* (2006.01)
*A61B 5/151* (2006.01)
*A61B 5/154* (2006.01)
*B01L 3/00* (2006.01)
*A61B 5/1455* (2006.01)
*A61B 5/1486* (2006.01)
*A61B 10/00* (2006.01)
*G01N 33/18* (2006.01)

(52) U.S. Cl.
CPC ......... *A61B 5/14532* (2013.01); *A61B 5/14539* (2013.01); *A61B 5/14546* (2013.01); *A61B 5/151* (2013.01); *A61B 5/154* (2013.01); *A61B 5/150022* (2013.01); *A61B 5/15105* (2013.01); *A61B 5/15142* (2013.01); *A61B 5/150213* (2013.01); *A61B 5/150221* (2013.01); *A61B 5/150229* (2013.01); *A61B 5/150343* (2013.01); *A61B 5/150412* (2013.01); *A61B 5/150503* (2013.01); *A61B 5/150755* (2013.01); *B01L 3/502753* (2013.01); *G01N 33/1826* (2013.01); *A61B 5/1455* (2013.01); *A61B 5/1486* (2013.01); *A61B 5/150969* (2013.01); *A61B 5/150984* (2013.01); *A61B 10/0045* (2013.01); *A61B 2562/0295* (2013.01); *B01L 2300/0672* (2013.01); *B01L 2300/0681* (2013.01); *B01L 2300/087* (2013.01); *B01L 2300/0816* (2013.01); *B01L 2300/0874* (2013.01); *B01L 2400/049* (2013.01); *B01L 2400/0655* (2013.01); *B01L 2400/0688* (2013.01); *G01N 33/18* (2013.01)

(56) References Cited

U.S. PATENT DOCUMENTS

| | | |
|---|---|---|
| 3,339,546 A | 9/1967 | Chen |
| 3,551,554 A | 12/1970 | Herschler |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,761,013 A | 9/1973 | Schuster |
| 3,908,657 A | 9/1975 | Kowarski |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,329,999 A | 5/1982 | Phillips |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,615,697 A | 10/1986 | Robinson |
| 4,621,268 A | 11/1986 | Keeling et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,863,970 A | 9/1989 | Patel et al. |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,279,294 A | 1/1994 | Anderson et al. |
| 5,320,607 A | 6/1994 | Ishibashi |
| 5,379,895 A | 1/1995 | Foslien |
| 5,402,798 A | 4/1995 | Swierczek et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,807,375 A | 9/1998 | Gross et al. |
| 5,811,108 A | 9/1998 | Goeringer |
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,027,459 A | 2/2000 | Shain et al. |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |

(56) References Cited

U.S. PATENT DOCUMENTS

| | | | |
|---|---|---|---|
| 6,080,116 A | 6/2000 | Erickson et al. | |
| 6,083,196 A | 7/2000 | Trautman et al. | |
| 6,091,975 A | 7/2000 | Daddona et al. | |
| 6,093,156 A | 7/2000 | Cunningham et al. | |
| 6,099,484 A | 8/2000 | Douglas et al. | |
| 6,107,102 A | 8/2000 | Ferrari | |
| 6,126,899 A | 10/2000 | Woudenberg et al. | |
| 6,132,449 A | 10/2000 | Lum et al. | |
| 6,132,702 A | 10/2000 | Witt et al. | |
| 6,152,889 A | 11/2000 | Sopp et al. | |
| 6,152,942 A | 11/2000 | Brenneman et al. | |
| 6,155,992 A | 12/2000 | Henning et al. | |
| 6,162,639 A | 12/2000 | Douglas | |
| 6,190,315 B1 | 2/2001 | Kost et al. | |
| 6,192,890 B1 | 2/2001 | Levy et al. | |
| 6,203,504 B1 | 3/2001 | Latterell et al. | |
| 6,206,841 B1 | 3/2001 | Cunningham et al. | |
| 6,219,574 B1 | 4/2001 | Cormier et al. | |
| 6,228,100 B1 | 5/2001 | Schraga | |
| 6,230,051 B1 | 5/2001 | Cormier et al. | |
| 6,234,990 B1 | 5/2001 | Rowe et al. | |
| 6,235,313 B1 | 5/2001 | Mathiowitz et al. | |
| 6,252,129 B1 | 6/2001 | Coffee | |
| 6,267,724 B1 | 7/2001 | Taylor | |
| 6,283,926 B1 | 9/2001 | Cunningham et al. | |
| 6,306,104 B1 | 10/2001 | Cunningham et al. | |
| 6,306,993 B1 | 10/2001 | Rothbard et al. | |
| 6,309,887 B1 | 10/2001 | Ray | |
| 6,319,210 B1 | 11/2001 | Douglas et al. | |
| 6,322,574 B1 | 11/2001 | Lloyd | |
| 6,332,871 B1 | 12/2001 | Douglas et al. | |
| 6,334,856 B1 | 1/2002 | Allen et al. | |
| 6,340,354 B1 | 1/2002 | Rambin | |
| 6,349,229 B1 | 2/2002 | Watanabe et al. | |
| 6,349,850 B1 | 2/2002 | Cheikh | |
| 6,361,944 B1 | 3/2002 | Mirkin et al. | |
| 6,364,890 B1 | 4/2002 | Lum et al. | |
| 6,379,324 B1 | 4/2002 | Gartstein et al. | |
| 6,391,471 B1 | 5/2002 | Hiraoka et al. | |
| 6,406,919 B1 | 6/2002 | Tyrrell | |
| 6,409,679 B2 | 6/2002 | Pyo | |
| 6,436,078 B1 | 8/2002 | Svedman | |
| 6,440,096 B1 | 8/2002 | Lastovich et al. | |
| 6,455,324 B1 | 9/2002 | Douglas | |
| 6,461,644 B1 | 10/2002 | Jackson et al. | |
| 6,464,649 B1 | 10/2002 | Duchon et al. | |
| 6,465,002 B1 | 10/2002 | Mathiowitz et al. | |
| 6,485,439 B1 | 11/2002 | Roe et al. | |
| 6,485,703 B1 | 11/2002 | Cote et al. | |
| 6,491,657 B2 | 12/2002 | Rowe et al. | |
| 6,491,902 B2 | 12/2002 | Shefer et al. | |
| 6,501,976 B1 | 12/2002 | Sohrab | |
| 6,502,697 B1 | 1/2003 | Crampton et al. | |
| 6,503,209 B2 | 1/2003 | Hakky et al. | |
| 6,503,231 B1 | 1/2003 | Prausnitz et al. | |
| 6,506,168 B1 | 1/2003 | Fathallah et al. | |
| 6,527,716 B1 | 3/2003 | Eppstein | |
| 6,532,386 B2 | 3/2003 | Sun et al. | |
| 6,537,243 B1 | 3/2003 | Henning et al. | |
| 6,537,264 B1 | 3/2003 | Cormier et al. | |
| 6,538,089 B1 | 3/2003 | Samra et al. | |
| 6,540,675 B2 | 4/2003 | Aceti et al. | |
| 6,548,264 B1 | 4/2003 | Tan et al. | |
| 6,558,361 B1 | 5/2003 | Yeshurun | |
| 6,562,014 B2 | 5/2003 | Lin et al. | |
| 6,589,562 B1 | 7/2003 | Shefer et al. | |
| 6,591,124 B2 | 7/2003 | Sherman et al. | |
| 6,602,205 B1 | 8/2003 | Erickson et al. | |
| 6,603,987 B2 | 8/2003 | Whitson | |
| 6,607,495 B1 | 8/2003 | Skalak et al. | |
| 6,607,513 B1 | 8/2003 | Down et al. | |
| 6,611,707 B1 | 8/2003 | Prausnitz et al. | |
| 6,614,522 B1 | 9/2003 | Sopp et al. | |
| 6,620,123 B1 | 9/2003 | Mitragotri et al. | |
| 6,624,882 B2 | 9/2003 | Sopp et al. | |
| 6,626,884 B1 | 9/2003 | Dillon et al. | |
| 6,652,478 B1 | 11/2003 | Gartstein et al. | |
| 6,656,147 B1 | 12/2003 | Gertsek et al. | |
| 6,660,527 B2 | 12/2003 | Stroup | |
| 6,669,961 B2 | 12/2003 | Kim et al. | |
| 6,678,554 B1 | 1/2004 | Sun et al. | |
| 6,685,921 B2 | 2/2004 | Lawlor | |
| 6,689,100 B2 | 2/2004 | Connelly et al. | |
| 6,696,075 B2 | 2/2004 | Mathiowitz et al. | |
| 6,706,000 B2 | 3/2004 | Perez et al. | |
| 6,706,159 B2 | 3/2004 | Moerman et al. | |
| 6,712,776 B2 | 3/2004 | Latterell et al. | |
| 6,741,877 B1 | 5/2004 | Shults et al. | |
| 6,743,211 B1 | 6/2004 | Prausnitz et al. | |
| 6,749,575 B2 | 6/2004 | Matriano et al. | |
| 6,765,081 B2 | 7/2004 | Lin et al. | |
| 6,766,817 B2 | 7/2004 | da Silva | |
| 6,768,920 B2 | 7/2004 | Lange et al. | |
| 6,783,502 B2 | 8/2004 | Orloff et al. | |
| 6,786,874 B2 | 9/2004 | Grace et al. | |
| 6,793,633 B2 | 9/2004 | Douglas et al. | |
| 6,798,920 B1 | 9/2004 | Wells et al. | |
| 6,800,122 B2 | 10/2004 | Anderson et al. | |
| 6,811,090 B2 | 11/2004 | Yogi et al. | |
| 6,814,760 B2 | 11/2004 | Anderson et al. | |
| 6,825,161 B2 | 11/2004 | Shefer et al. | |
| 6,826,426 B2 | 11/2004 | Lange et al. | |
| 6,837,858 B2 | 1/2005 | Cunningham et al. | |
| 6,855,133 B2 | 2/2005 | Svedman | |
| 6,860,873 B2 | 3/2005 | Allen et al. | |
| 6,878,120 B2 | 4/2005 | Roe et al. | |
| 6,896,666 B2 | 5/2005 | Kochamba | |
| 6,899,851 B2 | 5/2005 | Allen et al. | |
| 6,908,448 B2 | 6/2005 | Redding, Jr. | |
| 6,918,404 B2 | 7/2005 | Dias da Silva | |
| 6,918,901 B1 | 7/2005 | Theeuwes et al. | |
| 6,923,764 B2 | 8/2005 | Aceti et al. | |
| 6,931,277 B1 | 8/2005 | Yuzhakov et al. | |
| 6,940,591 B2 | 9/2005 | Sopp et al. | |
| 6,952,604 B2 | 10/2005 | DeNuzzio et al. | |
| 6,969,359 B2 | 11/2005 | Duchon et al. | |
| 6,990,367 B2 | 1/2006 | Kiser et al. | |
| 6,997,886 B2 | 2/2006 | Latterell et al. | |
| 7,001,343 B2 | 2/2006 | Erickson et al. | |
| 7,001,344 B2 | 2/2006 | Freeman et al. | |
| 7,004,928 B2 | 2/2006 | Aceti et al. | |
| 7,008,384 B2 | 3/2006 | Tapper | |
| 7,014,615 B2 | 3/2006 | Erickson et al. | |
| 7,037,277 B1 | 5/2006 | Smith et al. | |
| 7,041,067 B2 | 5/2006 | Sopp et al. | |
| 7,041,068 B2 | 5/2006 | Freeman et al. | |
| 7,047,070 B2 | 5/2006 | Wilkinson et al. | |
| 7,066,586 B2 | 6/2006 | da Silva | |
| 7,066,885 B2 | 6/2006 | Erickson et al. | |
| 7,097,631 B2 | 8/2006 | Trautman et al. | |
| 7,133,717 B2 | 11/2006 | Coston et al. | |
| 7,137,957 B2 | 11/2006 | Erickson et al. | |
| 7,150,755 B2 | 12/2006 | Levaughn et al. | |
| 7,174,199 B2 | 2/2007 | Berner et al. | |
| 7,182,910 B2 | 2/2007 | Allen et al. | |
| 7,235,056 B2 | 6/2007 | Duchon et al. | |
| 7,247,144 B2 | 7/2007 | Douglas et al. | |
| 7,264,627 B2 | 9/2007 | Perez | |
| 7,316,671 B2 | 1/2008 | Lastovich et al. | |
| 7,335,166 B2 | 2/2008 | Faupel et al. | |
| 7,344,499 B1 | 3/2008 | Prausnitz et al. | |
| 7,344,587 B2 | 3/2008 | Khan et al. | |
| 7,374,545 B2 | 5/2008 | Alroy | |
| 7,374,949 B2 | 5/2008 | Kuriger | |
| 7,402,441 B2 | 7/2008 | Lowe et al. | |
| 7,413,868 B2 | 8/2008 | Kauvar et al. | |
| 7,422,567 B2 | 9/2008 | Lastovich et al. | |
| 7,429,258 B2 | 9/2008 | Angel et al. | |
| 7,537,590 B2 | 5/2009 | Santini et al. | |
| 7,544,185 B2 | 6/2009 | Bengtsson | |
| 7,575,717 B2 | 8/2009 | Cooke et al. | |
| 7,585,278 B2 | 9/2009 | Aceti et al. | |
| 7,585,412 B2 * | 9/2009 | Gorsuch et al. ......... 210/500.23 | |
| 7,631,760 B2 | 12/2009 | Guelzow et al. | |

(56) References Cited

U.S. PATENT DOCUMENTS

| | | | |
|---|---|---|---|
| 7,758,518 B2 | 7/2010 | Perez et al. | |
| 7,767,017 B2 | 8/2010 | Lahann et al. | |
| 7,811,302 B2 | 10/2010 | Steg | |
| 7,883,473 B2 | 2/2011 | LeVaughn et al. | |
| 7,896,830 B2 * | 3/2011 | Gura et al. | 604/5.04 |
| 7,942,827 B2 | 5/2011 | Mir et al. | |
| 7,947,772 B2 | 5/2011 | Lahann et al. | |
| 8,043,480 B2 | 10/2011 | Lahann et al. | |
| 8,052,849 B2 | 11/2011 | Lahann et al. | |
| 8,075,826 B2 | 12/2011 | Lastovich et al. | |
| 8,133,191 B2 | 3/2012 | Rosenberg et al. | |
| 8,187,708 B2 | 5/2012 | Lahann et al. | |
| 8,202,240 B2 * | 6/2012 | Felt et al. | 604/6.04 |
| 8,241,651 B2 | 8/2012 | Lahann | |
| 8,246,582 B2 | 8/2012 | Angel et al. | |
| 8,344,028 B2 | 1/2013 | Xu et al. | |
| 8,523,894 B2 | 9/2013 | Schmelzeisen-Redeker et al. | |
| 8,561,795 B2 | 10/2013 | Schott | |
| 8,808,202 B2 | 8/2014 | Brancazio | |
| 8,821,412 B2 | 9/2014 | Gonzalez-Zugasti et al. | |
| 8,827,971 B2 | 9/2014 | Chickering, III et al. | |
| 8,900,180 B2 | 12/2014 | Wolter et al. | |
| 9,033,898 B2 | 5/2015 | Chickering, III et al. | |
| 2001/0005772 A1 | 6/2001 | Kisakibaru | |
| 2002/0010414 A1 | 1/2002 | Coston et al. | |
| 2002/0013538 A1 | 1/2002 | Teller | |
| 2002/0065453 A1 | 5/2002 | Lesho et al. | |
| 2002/0077584 A1 | 6/2002 | Lin et al. | |
| 2002/0082543 A1 | 6/2002 | Park et al. | |
| 2002/0099308 A1 | 7/2002 | Bojan et al. | |
| 2002/0099356 A1 | 7/2002 | Unger et al. | |
| 2002/0115967 A1 | 8/2002 | Svedman | |
| 2002/0119136 A1 | 8/2002 | Johansen | |
| 2002/0130042 A1 | 9/2002 | Moerman et al. | |
| 2002/0138049 A1 | 9/2002 | Allen | |
| 2002/0168290 A1 | 11/2002 | Yuzhakov et al. | |
| 2002/0169393 A1 | 11/2002 | Cunningham et al. | |
| 2002/0169394 A1 | 11/2002 | Eppstein et al. | |
| 2002/0169411 A1 | 11/2002 | Sherman et al. | |
| 2002/0187556 A1 | 12/2002 | Shartle et al. | |
| 2002/0188221 A1 | 12/2002 | Sohrab | |
| 2003/0040682 A1 | 2/2003 | Tapper | |
| 2003/0055326 A1 | 3/2003 | Sohrab | |
| 2003/0083645 A1 | 5/2003 | Angel et al. | |
| 2003/0083685 A1 | 5/2003 | Freeman et al. | |
| 2003/0100846 A1 | 5/2003 | Custer et al. | |
| 2003/0109807 A1 | 6/2003 | Knoll | |
| 2003/0113540 A1 | 6/2003 | Anderson et al. | |
| 2003/0135158 A1 | 7/2003 | Gonnelli | |
| 2003/0135167 A1 | 7/2003 | Gonnelli | |
| 2003/0135201 A1 | 7/2003 | Gonnelli | |
| 2003/0135333 A1 | 7/2003 | Aceti et al. | |
| 2003/0143746 A1 | 7/2003 | Sage | |
| 2003/0159615 A1 | 8/2003 | Anderson et al. | |
| 2003/0162304 A1 | 8/2003 | Dority et al. | |
| 2003/0181863 A1 | 9/2003 | Ackley et al. | |
| 2003/0187394 A1 | 10/2003 | Wilkinson et al. | |
| 2003/0187395 A1 | 10/2003 | Gabel et al. | |
| 2003/0195398 A1 | 10/2003 | Suzuki et al. | |
| 2003/0204148 A1 | 10/2003 | Lange et al. | |
| 2003/0208138 A1 | 11/2003 | Olson | |
| 2003/0212344 A1 | 11/2003 | Yuzhakov et al. | |
| 2003/0212345 A1 | 11/2003 | McAllister et al. | |
| 2003/0212347 A1 | 11/2003 | Sohrab | |
| 2003/0212423 A1 | 11/2003 | Pugh et al. | |
| 2003/0228367 A1 | 12/2003 | Mathiowitz et al. | |
| 2004/0010207 A1 | 1/2004 | Flaherty et al. | |
| 2004/0058458 A1 | 3/2004 | Anker et al. | |
| 2004/0096959 A1 | 5/2004 | Stiene et al. | |
| 2004/0098009 A1 | 5/2004 | Boecker et al. | |
| 2004/0106904 A1 | 6/2004 | Gonnelli et al. | |
| 2004/0171980 A1 | 9/2004 | Mitragotri et al. | |
| 2004/0199103 A1 | 10/2004 | Kwon | |
| 2004/0204744 A1 | 10/2004 | Penner et al. | |
| 2004/0236250 A1 | 11/2004 | Hodges et al. | |
| 2004/0247016 A1 | 12/2004 | Faries | |
| 2004/0249310 A1 | 12/2004 | Shartle et al. | |
| 2004/0253185 A1 | 12/2004 | Herweck et al. | |
| 2005/0015055 A1 | 1/2005 | Yang | |
| 2005/0019902 A1 | 1/2005 | Mathies et al. | |
| 2005/0027176 A1 | 2/2005 | Xie | |
| 2005/0027308 A1 | 2/2005 | Davis et al. | |
| 2005/0038669 A1 | 2/2005 | Sachdeva et al. | |
| 2005/0054907 A1 | 3/2005 | Page et al. | |
| 2005/0064529 A1 | 3/2005 | Kwon | |
| 2005/0069925 A1 | 3/2005 | Ford et al. | |
| 2005/0070819 A1 | 3/2005 | Poux et al. | |
| 2005/0085838 A1 | 4/2005 | Thompson et al. | |
| 2005/0106066 A1 * | 5/2005 | Saltsman et al. | 422/57 |
| 2005/0106713 A1 | 5/2005 | Phan et al. | |
| 2005/0137481 A1 | 6/2005 | Sheard et al. | |
| 2005/0137531 A1 | 6/2005 | Prausnitz et al. | |
| 2005/0137536 A1 | 6/2005 | Gonnelli | |
| 2005/0172852 A1 | 8/2005 | Anderson et al. | |
| 2005/0182307 A1 | 8/2005 | Currie et al. | |
| 2005/0196747 A1 | 9/2005 | Stiene | |
| 2005/0201974 A1 | 9/2005 | Schestopol et al. | |
| 2005/0203360 A1 | 9/2005 | Brauker et al. | |
| 2005/0215923 A1 | 9/2005 | Wiegel | |
| 2005/0221276 A1 | 10/2005 | Rozakis et al. | |
| 2005/0228313 A1 | 10/2005 | Kaler et al. | |
| 2005/0245844 A1 | 11/2005 | Mace et al. | |
| 2005/0249672 A1 | 11/2005 | Bolbot | |
| 2005/0251152 A1 | 11/2005 | Herweck et al. | |
| 2005/0261632 A1 | 11/2005 | Xu | |
| 2005/0261639 A1 | 11/2005 | Herweck | |
| 2006/0001551 A1 | 1/2006 | Kraft et al. | |
| 2006/0004271 A1 | 1/2006 | Peyser et al. | |
| 2006/0004303 A1 | 1/2006 | Weidenhaupt et al. | |
| 2006/0030790 A1 | 2/2006 | Braig et al. | |
| 2006/0036187 A1 | 2/2006 | Vos et al. | |
| 2006/0058602 A1 | 3/2006 | Kwiatkowski et al. | |
| 2006/0089566 A1 | 4/2006 | DeHart | |
| 2006/0142651 A1 | 6/2006 | Brister et al. | |
| 2006/0200046 A1 | 9/2006 | Windus-Smith et al. | |
| 2006/0228259 A1 | 10/2006 | Samsoondar | |
| 2006/0258959 A1 | 11/2006 | Sode | |
| 2006/0264779 A1 | 11/2006 | Kemp et al. | |
| 2006/0264782 A1 | 11/2006 | Holmes et al. | |
| 2007/0004989 A1 | 1/2007 | Dhillon | |
| 2007/0016446 A1 | 1/2007 | Brown | |
| 2007/0027427 A1 | 2/2007 | Trautman et al. | |
| 2007/0031283 A1 | 2/2007 | Davis et al. | |
| 2007/0036686 A1 | 2/2007 | Hatamian et al. | |
| 2007/0046476 A1 | 3/2007 | Hinkamp | |
| 2007/0054119 A1 | 3/2007 | Garstecki et al. | |
| 2007/0066934 A1 | 3/2007 | Etheredge et al. | |
| 2007/0078414 A1 | 4/2007 | McAllister et al. | |
| 2007/0092637 A1 | 4/2007 | Brown et al. | |
| 2007/0100219 A1 | 5/2007 | Sweitzer et al. | |
| 2007/0105176 A1 | 5/2007 | Ibey et al. | |
| 2007/0112180 A1 | 5/2007 | Gray et al. | |
| 2007/0123801 A1 | 5/2007 | Goldberger et al. | |
| 2007/0129618 A1 | 6/2007 | Goldberger et al. | |
| 2007/0161926 A1 | 7/2007 | Imamura et al. | |
| 2007/0161964 A1 | 7/2007 | Yuzhakov | |
| 2007/0167340 A1 | 7/2007 | Barthel et al. | |
| 2007/0173740 A1 | 7/2007 | Chan et al. | |
| 2007/0179404 A1 | 8/2007 | Escutia et al. | |
| 2007/0185432 A1 | 8/2007 | Etheredge et al. | |
| 2007/0208275 A1 | 9/2007 | Vinogradov et al. | |
| 2007/0213638 A1 | 9/2007 | Herbrechtsmeier et al. | |
| 2007/0225676 A1 | 9/2007 | Prausnitz et al. | |
| 2007/0231355 A1 | 10/2007 | Quadir et al. | |
| 2007/0232956 A1 | 10/2007 | Harman et al. | |
| 2007/0233199 A1 | 10/2007 | Moore et al. | |
| 2007/0237800 A1 | 10/2007 | Lahann | |
| 2007/0238943 A1 | 10/2007 | Poulsen et al. | |
| 2007/0249962 A1 | 10/2007 | Alden et al. | |
| 2008/0009763 A1 | 1/2008 | Chiou et al. | |
| 2008/0014627 A1 | 1/2008 | Merchant et al. | |
| 2008/0051689 A1 | 2/2008 | Gura et al. | |
| 2008/0077430 A1 | 3/2008 | Singer et al. | |
| 2008/0081695 A1 | 4/2008 | Patchen | |

(56) References Cited

U.S. PATENT DOCUMENTS

| | | |
|---|---|---|
| 2008/0086051 A1 | 4/2008 | Voegele |
| 2008/0099478 A1 | 5/2008 | Gleich |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelmann et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183144 A1 | 7/2008 | Trautmann et al. |
| 2008/0200838 A1 | 8/2008 | Goldberger et al. |
| 2008/0220411 A1 | 9/2008 | McNaughton et al. |
| 2008/0221407 A1 | 9/2008 | Baker |
| 2008/0269666 A1 | 10/2008 | Wang et al. |
| 2008/0275327 A1 | 11/2008 | Faarbaek et al. |
| 2008/0281290 A1 | 11/2008 | Yodfat et al. |
| 2008/0300508 A1 | 12/2008 | Tomer |
| 2008/0319347 A1 | 12/2008 | Keren |
| 2009/0036795 A1 | 2/2009 | Duineveld et al. |
| 2009/0043250 A1 | 2/2009 | Gonnelli |
| 2009/0054813 A1 | 2/2009 | Freeman et al. |
| 2009/0099478 A1 | 4/2009 | Cassells et al. |
| 2009/0099529 A1 | 4/2009 | Anderson et al. |
| 2009/0105614 A1 | 4/2009 | Momose et al. |
| 2009/0124994 A1 | 5/2009 | Roe |
| 2009/0182306 A1 | 7/2009 | Lee et al. |
| 2009/0187160 A1 | 7/2009 | McAllister et al. |
| 2009/0198189 A1 | 8/2009 | Simons et al. |
| 2009/0198215 A1 | 8/2009 | Chong et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0121368 A1 | 5/2010 | Kim et al. |
| 2010/0147763 A1* | 6/2010 | Tsou et al. ............... 210/500.21 |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0292191 A1 | 11/2010 | Mainx et al. |
| 2010/0324449 A1 | 12/2010 | Rostaing et al. |
| 2010/0324451 A1 | 12/2010 | Ishibashi et al. |
| 2011/0003770 A1 | 1/2011 | Eek |
| 2011/0009847 A1 | 1/2011 | Levinson et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0172508 A1 | 7/2011 | Chickering, III et al. |
| 2011/0172510 A1* | 7/2011 | Chickering et al. .......... 600/317 |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0123297 A1 | 5/2012 | Brancazio |
| 2012/0271125 A1 | 10/2012 | Bernstein et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0138058 A9 | 5/2013 | Gonzalez-Zugasti, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |

FOREIGN PATENT DOCUMENTS

| | | |
|---|---|---|
| CN | 1501788 A | 6/2004 |
| CN | 1524493 A | 9/2004 |
| CN | 1551743 A | 12/2004 |
| CN | 1753646 A | 3/2006 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |
| EP | 0 250 693 A1 | 1/1988 |
| EP | 0 365 196 A2 | 4/1990 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 2 064 993 A1 | 6/2009 |
| EP | 2 077 128 A1 | 7/2009 |
| GB | 2153223 A | 8/1985 |
| JP | 63-108264 | 5/1988 |
| JP | 5-63506 | 8/1993 |
| JP | 7-255706 | 10/1995 |
| JP | 2000-116629 | 4/2000 |
| JP | 2002-272710 | 9/2002 |
| JP | 2004-8413 | 1/2004 |
| JP | 2004-532079 A | 10/2004 |
| JP | 2005-011364 A | 1/2005 |
| JP | 2005-211189 | 8/2005 |
| JP | 2005-525141 | 8/2005 |
| JP | 2006-15148 | 1/2006 |
| JP | 2006-109894 | 4/2006 |
| JP | 2006-521555 | 9/2006 |
| JP | 2007-209747 | 8/2007 |
| JP | 2008-099992 | 5/2008 |
| JP | 2009-504273 | 2/2009 |
| WO | WO 92/02175 A1 | 2/1992 |
| WO | WO 95/10223 A2 | 4/1995 |
| WO | WO 95/15783 A1 | 6/1995 |
| WO | WO 97/08987 A1 | 3/1997 |
| WO | WO 97/10745 A1 | 3/1997 |
| WO | WO 97/34587 A2 | 9/1997 |
| WO | WO 97/48442 A1 | 12/1997 |
| WO | WO 98/24366 A2 | 6/1998 |
| WO | WO 99/27852 A1 | 6/1999 |
| WO | WO 00/35357 A1 | 6/2000 |
| WO | WO 00/35530 A1 | 6/2000 |
| WO | WO 00/74763 A2 | 12/2000 |
| WO | WO 01/43643 A1 | 6/2001 |

(56) References Cited

FOREIGN PATENT DOCUMENTS

| WO | WO 01/93946 A1 | 12/2001 |
|----|----|----|
| WO | WO 02/00101 A2 | 1/2002 |
| WO | WO 02/05890 A2 | 1/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 03/020134 A2 | 3/2003 |
| WO | WO 03/026611 A2 | 4/2003 |
| WO | WO 03/030984 A2 | 4/2003 |
| WO | WO 03/037407 A1 | 5/2003 |
| WO | WO 03/039632 A2 | 5/2003 |
| WO | WO 03/070099 A1 | 8/2003 |
| WO | WO 03/082091 A2 | 10/2003 |
| WO | WO 03/088851 A1 | 10/2003 |
| WO | WO 03/099123 A1 | 12/2003 |
| WO | WO 2004/022133 A2 | 3/2004 |
| WO | WO 2004/085995 A2 | 10/2004 |
| WO | WO 2005/000118 A1 | 1/2005 |
| WO | WO 2005/023111 A1 | 3/2005 |
| WO | WO 2005/025413 A2 | 3/2005 |
| WO | WO 2004/006982 A3 | 4/2005 |
| WO | WO 2005/084534 A1 | 9/2005 |
| WO | WO 2005/107594 A2 | 11/2005 |
| WO | WO 2005/123173 A1 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/111741 A1 | 10/2006 |
| WO | WO 2006/121510 A2 | 11/2006 |
| WO | WO 2006/128034 A1 | 11/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/079530 A1 | 7/2007 |
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A2 | 9/2007 |
| WO | WO 2007/115291 A2 | 10/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/081444 A2 | 7/2008 |
| WO | WO 2008/153930 A1 | 12/2008 |
| WO | WO 2009/004627 A3 | 1/2009 |
| WO | WO 2009/011138 A1 | 1/2009 |
| WO | WO 2009/055693 A2 | 4/2009 |
| WO | WO 2009/071775 A1 | 6/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/110916 A2 | 9/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/064802 A1 | 5/2012 |

OTHER PUBLICATIONS

Chinese Office Action mailed Nov. 28, 2013 for Application No. 201080017376.3 and English translation thereof.
European Office Action mailed Nov. 26, 2013 for Application No. 10708432.9.
European Office Action mailed Apr. 11, 2013 for Application No. 10777165.1.
Chinese Office Action mailed Jun. 9, 2013 for Application No. 201080055393.6 and English translation thereof.
European Office Action mailed Aug. 14, 2013 for Application No. 10776881.4.
European Office Action mailed Jul. 29, 2013 for Application No. 11700881.3.
Chinese Office Action mailed Jun. 4, 2013 for Application No. 201080017375.9 and English translation thereof.
European Office Action mailed May 8, 2013 for Application No. 10708434.5.
European Office Action mailed Dec. 10, 2013 for Application No. 11746127.7.
European Office Action mailed Sep. 2, 2013 for Application No. 11700780.7.
International Preliminary Report on Patentability for PCT/US2009/046333 mailed Aug. 31, 2010.
International Search Report and Written Opinion for PCT/US2009/046333 mailed Dec. 9, 2009.
Invitation to Pay Additional Fees for PCT/US2009/046333 mailed Sep. 28, 2009.
Invitation to Restrict or Pay Additional Fees, and Where Applicable, Protest Fees for PCT/US2009/046333 mailed Jul. 8, 2010.
International Search Report and Written Opinion for PCT/US2010/000623 mailed Sep. 22, 2010.
Invitation to Pay Additional Fees for PCT/US2010/000623 mailed Jun. 28, 2010.
International Search Report and Written Opinion for PCT/US2010/000630 mailed Jun. 16, 2011.
Invitation to Pay Additional Fees for PCT/US2010/000630 mailed Jun. 9, 2010.
International Preliminary Report on Patentability for PCT/US2010/000624 mailed Aug. 5, 2011.
International Search Report and Written Opinion for PCT/US2010/000624 mailed Aug. 18, 2010.
Invitation to Pay Additional Fees for PCT/US2010/000624 mailed Jun. 2, 2010.
Invitation to Restrict or Pay Additional Fees, and Where Applicable, Protest Fees for PCT/US2010/000624 mailed Jun. 20, 2011.
International PreliminaryReport on Patentability for PCT/US2010/054723 mailed May 10, 2012.
International Search Report and Written for PCT/US2010/054723 mailed Jul. 12, 2011.
Invitation to Pay Additional Fees for PCT/US2010/054723 mailed Mar. 1, 2011.
International Preliminary Report on Patentability for PCT/US2010/054741 mailed May 10, 2012.
International Search Report and Written Opinion for PCT/US2010/054741 mailed Apr. 27, 2011.
Invitation to Pay Additional Fees for PCT/US2010/054741 mailed Feb. 21, 2011.
International Preliminary Report on Patentability for PCT/US2010/054725 mailed May 10, 2012.
International Search Report and Written Opinion for PCT/US2010/054725 mailed Jun. 8, 2011.
Invitation to Pay Additional Fees for PCT/US2010/054725 mailed Feb. 21, 2011.
International Preliminary Report on Patentability for PCT/US2011/022967 mailed Aug. 9, 2012.
International Search Report and Written Opinion for PCT/US2011/022967 mailed Jul. 7, 2011.
International Preliminary Report on Patentability for PCT/US2010/003045 mailed Jun. 7, 2012.
International Search Report and Written for PCT/US2010/003045 mailed Jul. 27, 2011.
Invitation to Pay Additional Fees for PCT/US2010/003045 mailed Apr. 6, 2011.
International Preliminary Report on Patentabiltiy for PCT/US2011/021134 mailed Jul. 26, 2012.
International Search Report and Written Opinion for PCT/US2011/021134 mailed Oct. 27, 2011.
Invitation to Pay Additional Fees for PCT/US2011/021134 mailed Apr. 28, 2011.

(56) References Cited

OTHER PUBLICATIONS

International Preliminary Report on Patentability for PCT/US2010/000631 mailed Aug. 5, 2011.
International Search Report and Written Opinion for PCT/US2010/000631 mailed Aug. 4, 2010.
Invitation to Pay Additional Fees for PCT/US2010/000631 mailed Jun. 9, 2010.
Invitation to Restrict or Pay Additional Fees, and Where Applicable, Protest Fees for PCT/US2010/000631 mailed Jun. 20, 2011.
International Preliminary Report on Patentability for PCT/US2011/041430 mailed Jan. 10, 2013.
International Search Report and Written Opinion for PCT/US2011/041430 mailed Jan. 31, 2012.
Invitation to Pay Additional Fees for PCT/US2011/041430 mailed Nov. 4, 2011.
International Preliminary Report on Patentability for PCT/US2011/043698 mailed Feb. 7, 2013.
International Search Report and Written Opinion for PCT/US2011/043698 mailed Feb. 23, 2012.
International Preliminary Report on Patentability for PCT/US2011/044145 mailed Jan. 31, 2013.
International Search Report and Written Opinion for PCT/US2011/044145 mailed Dec. 2, 2011.
International Preliminary Report on Patentability for PCT/US2011/047565 mailed Feb. 28, 2013.
International Search Report and Written Opinion for PCT/US2011/047565 mailed Mar. 9, 2012.
Invitation to Pay Additional Fee for PCT/US2011/047565 mailed Dec. 2, 2011.
International Preliminary Report on Patentability for PCT/US2011/047581 mailed Feb. 28, 2013.
International Search Report and Written Opinion for PCT/US2011/047581 mailed Mar. 28, 2012.
International Preliminary Report mailed May 23, 2013 for PCT/US2011/059876.
International Search Report and Written Opinion for PCT/US2011/059876 mailed Feb. 22, 2012.
International Preliminary Report on Patentabiltiy for PCT/US2011/021131 mailed Jul. 26, 2012.
International Search Report and Written Opinion for PCT/US2011/021131 mailed Sep. 30, 2011.
Invitation to Pay Additional Fees for PCT/US2011/021131 mailed May 23, 2011.
International Preliminary Report on Patentabiltiy for PCT/US2012/035191 mailed Nov. 7, 2013.
International Search Report and Written Opinion mailed Oct. 4, 2012 in connection with PCT/US2012/035191.
Invitation to Pay Additional Fees mailed Aug. 17, 2012 in connection with PCT/US2012/035191.
International Preliminary Report on Patentabiltiy for PCT/US2012/035207 mailed Nov. 7, 2013.
International Search Report and Written Opinion mailed Oct. 4, 2012 in connection with PCT/US2012/035207.
Invitation to Pay Additional Fees mailed Aug. 17, 2012 in connection with PCT/US2012/035207.
International Preliminary Report on Patentabiltiy for PCT/US2012/035152 mailed Nov. 7, 2013.
International Search Report and Written Opinion for PCT/US2012/035152 mailed Aug. 17, 2012.
International Preliminary Report on Patentabiltiy for PCT/US2012/032846 mailed Oct. 24, 2013.
International Search Report and Written Opinion for PCT/US2012/032846 mailed Jul. 23, 2012.
International Preliminary Report on Patentability for PCT/US2012/035173 mailed Nov. 7, 2013.
International Search Report and Written Opinion mailed Oct. 4, 2012 in connection with PCT/US2012/035173.
Invitation to Pay Additional Fees mailed Aug. 17, 2012 in connection with PCT/US2012/035173.
Office Action mailed Dec. 7, 2012 for U.S. Appl. No. 12/478,756.
Office Action mailed Mar. 26, 2012 for U.S. Appl. No. 12/716,233.
Office Action mailed Jun. 21, 2012 for U.S. Appl. No. 12/716,229.
Office Action mailed May 14, 2013 for U.S. Appl. No. 12/716,229.
Office Action mailed Dec. 30, 2013 for U.S. Appl. No. 12/716,229.
Office Action mailed Apr. 30, 2013 for U.S. Appl. No. 12/915,735.
Office Action mailed Nov. 1, 2012 for U.S. Appl. No. 12/915,789.
Office Action mailed Aug. 30, 2013 for U.S. Appl. No. 12/915,789.
Office Action mailed Nov. 1, 2012 for U.S. Appl. No. 12/915,820.
Office Action mailed May 30, 2013 for U.S. Appl. No. 12/915,820.
Office Action mailed May 20, 2013 for U.S. Appl. No. 13/016,575.
Office Action mailed Jan. 2, 2014 for U.S. Appl. No. 13/016,575.
Office Action mailed Apr. 20, 2012 in connection with U.S. Appl. No. 12/953,744.
Office Action mailed Aug. 23, 2012 in connection with U.S. Appl. No. 12/953,744.
Office Action mailed Apr. 26, 2013 in connection with U.S. Appl. No. 12/953,744.
Office Action mailed Dec. 19, 2013 for U.S. Appl. No. 12/953,744.
Office Action mailed Dec. 28, 2012 for U.S. Appl. No. 13/166,611.
Office Action mailed Aug. 8, 2013 for U.S. Appl. No. 13/166,611.
Office Action mailed Dec. 22, 2011 in connection with U.S. Appl. No. 12/716,226.
Office Action mailed Jun. 20, 2012 in connection with U.S. Appl. No. 12/716,226.
Office Action mailed Jan. 31, 2013 for U.S. Appl. No. 13/166,451.
Office Action mailed Aug. 8, 2013 for U.S. Appl. No. 13/166,451.
Office Action mailed May 17, 2013 for U.S. Appl. No. 13/678,316.
Office Action mailed Apr. 9, 2013 for U.S. Appl. No. 13/208,770.
Office Action mailed Nov. 14, 2013 for U.S. Appl. No. 13/208,770.
Office Action mailed Sep. 11, 2013 for U.S. Appl. No. 13/208,808.
Office Action mailed Aug. 8, 2013 for U.S. Appl. No. 13/292,254.
Office Action mailed Nov. 25, 2013 for U.S. Appl. No. 13/292,254.
Office Action mailed Dec. 30, 2013 for U.S. Appl. No. 13/006,165.
Office Action mailed May 7, 2013 for U.S. Appl. No. 13/680,351.
Office Action mailed Sep. 27, 2013 for U.S. Appl. No. 13/680,351.
Office Action mailed Oct. 10, 2013 for U.S. Appl. No. 13/680,351.
Office Action mailed Jul. 18, 2013 for U.S. Appl. No. 13/456,394.
Office Action mailed Jan. 3, 2014 for U.S. Appl. No. 13/456,394.
[No Author Listed] Greiner Bio-One Preanalytics Catalogue. www.gbo.com/preanalytics. Feb. 2012. 76 pages.
[No Author Listed] Safe-T-Fill®: 100% Plastic Capillary Blood Collection Systems. RAM Scientific. [Month of publication not listed on copy.] 2003. Last accessed Jun. 28, 2012 at http//www.ramsci.com.
[No Author Listed] Sof-Tact Manual. Date Unknown. 57 pages. (After reasonable inquiry, the undersigned believes this manual was available beginning 2001, but cannot determine the exact date of this publication.The year of publication is sufficiently earlier than the effective U.S. filing date and priority date so that the particular month and year of publication is not in issue. See MPEP 609.04(a).).
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption-Mechanisms-Methodology. Bronaugh et al., eds. Marcell Dekker. 1989;3-12. (The year of publication is sufficiently earlier than the effective U.S. filing date and

(56) References Cited

OTHER PUBLICATIONS any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Matriano et al., Macroflux microprojection array patch technology: a new and efficient approach for intracutaneous immunization. Pharm Res. Jan. 2002;19(1):63-70.
McShane, Microcapsules as 'smart tattoo' glucose sensors: engineering systems with enzymes and glucose-binding sensing elements, Top Fluor. Spec., 2006, vol. 11, Glc. Sens., p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transdermal Drug Delivery by Application of Ultrasound. In: Encl. of Pharm. Tech., vol. 14, Swarbrick, J., Boylan, J., (Eds.), vol. 14, 103-122, 1996. (After reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990;12(2):O494-95. (The year of publication is sufficiently earlier than the effective U.S. filing date and any foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1):155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2006.
Whitesides et al., Soft lithography in biology and biochemistry. Annu Rev Biomed Eng. Aug. 2001;335-73.
Xia et al., Soft Lithography. Ann Rev Mater Sci. Aug. 1998;28:153-84.
Japanese Office Action mailed May 27, 2014 for Application No. 2011-552935.
Office Action mailed Jan. 15, 2014 for U.S. Appl. No. 12/915,735.
Office Action dated Oct. 31, 2014 for U.S. Appl. No. 12/915,735.
European Office Action mailed May 19, 2014 for Application No. 10777165.1.
Office Action mailed Jun. 18, 2014 for U.S. Appl. No. 12/915,789.
Chinese Office Action mailed Jan. 20, 2014 for Application No. 201080055393.6 and English translation thereof.
Chinese Office Action mailed Sep. 12, 2014 for Application No. CN 201080055393.6.
European Office Action mailed Sep. 29, 2014 for Application No. EP 10776881.4.
Japanese Office Action mailed Jul. 25, 2014 for Application No. JP 2012-537119.
Office Action mailed Jul. 21, 2014 for U.S. Appl. No. 12/915,820.
Office Action mailed Aug. 6, 2014 for U.S. Appl. No. 13/016,575.
Office Action mailed Jul. 8, 2014 for U.S. Appl. No. 12/953,744.
Chinese Office Action mailed Dec. 11, 2013 for Application No. 201180013047.6 and English translation thereof.
Chinese Office Action dated Aug. 29, 2014 for Application No. CN 201180013047.6.
European Office Action mailed Jul. 7, 2014 for Application No. EP 11700881.3.
Office Action mailed Jan. 16, 2014 for U.S. Appl. No. 13/006,177.
Chinese Office Action mailed Jan. 16, 2014 for Application No. 201080017375.9 and English translation thereof.
Japanese Office Action mailed May 27, 2014 for Application No. 2011-552936.
Office Action mailed Mar. 7, 2014 for U.S. Appl. No. 13/166,451.
Chinese Office Action mailed May 13, 2014 for Application No. 201180040283.7.
European Office Action mailed Jan. 16, 2014 for Application No. 11736245.9.
Examination Report dated Aug. 14, 2014 for Application No. EP 11736245.9.
Office Action mailed Apr. 11, 2014 for U.S. Appl. No. 13/183,789.
Office Action mailed May 29, 2014 for U.S. Appl. No. 13/208,770.
Office Action mailed Apr. 10, 2014 for U.S. Appl. No. 13/208,808.
European Office Action mailed Jul. 30, 2014 for Application No. EP 11785255.8.
Chinese Office Action mailed Mar. 11, 2014 for Application No. 201180013052.7.
European Office Action dated Aug. 28, 2014 for Application No. EP 11700780.7.
Japanese Office Action mailed Oct. 20, 2014 for Application No. JP 2012-549079.
Office Action mailed Jul. 31, 2014 for U.S. Appl. No. 13/456,394.
Office Action mailed May 20, 2014 for U.S. Appl. No. 13/456,505.
Office Action mailed Oct. 9, 2014 for U.S. Appl. No. 13/443,016.
Office Action mailed Sep. 22, 2014 for U.S. Appl. No. 13/456,546.
Chinese Office Action mailed Oct. 20, 2014 for Application No. CN 201080017376.3.
European Office Action mailed Feb. 26, 2015 for Application No. EP 10708432.9.
Japanese Office Action mailed Apr. 27, 2015 for Application No. 2011-552935.
European Office Action mailed Feb. 26, 2015 for Application No. EP 10776880.6.
Chinese Office Action mailed May 12, 2015 for Application No. 201080055393.6.
Chinese Office Action mailed May 11, 2015 for Application No. 201180013047.6.
Japanese Office Action mailed Nov. 5, 2014 for Application No. JP 2012-549080.
Japanese Office Action mailed Apr. 27, 2015 for Application No. 2011-552936.
Chinese Office Action mailed Feb. 2, 2015 for Application No. 201180040283.7.
European Office Action mailed Feb. 25, 2015 for Application No. EP 11736245.9.
European Office Action mailed Jan. 9, 2015 for Application No. 11746127.7.
Chinese Office Action mailed Sep. 30, 2014 for Application No. 201180060903.3.
European Office Action mailed Feb. 19, 2015 for Application No. EP 11785255.8.
Chinese Office Action mailed Nov. 19, 2014 for Application No. 201180013052.7.
Chinese Office Action mailed Mar. 24, 2015 for Application No. 201280021297.9.
Chinese Office Action mailed Mar. 24, 2015 for Application No. 201280021299.8.
Office Action mailed Feb. 23, 2015 for U.S. Appl. No. 12/716,229.
Office Action mailed Apr. 22, 2015 for U.S. Appl. No. 12/915,789.
Office Action mailed May 19, 2015 for U.S. Appl. No. 12/915,820.
Office Action mailed Mar. 3, 2015 for U.S. Appl. No. 12/953,744.
Office Action mailed Nov. 24, 2014 for U.S. Appl. No. 13/006,177.

(56) References Cited

OTHER PUBLICATIONS

Office Action mailed Jan. 15, 2015 for U.S. Appl. No. 12/716,226.
Final Office Action mailed Nov. 12, 2014 for U.S. Appl. No. 13/166,451.
Office Action mailed May 29, 2015 for U.S. Appl. No. 13/812,248.
Office Action mailed Jan. 27, 2015 for U.S. Appl. No. 13/183,789.
Office Action mailed Dec. 9, 2014 for U.S. Appl. No. 13/208,770.
Office Action mailed Nov. 20, 2014 for U.S. Appl. No. 13/208,808.
Final Office Action mailed Nov. 24, 2014 for U.S. Appl. No. 13/006,165.
Office Action mailed Feb. 27, 2015 for U.S. Appl. No. 13/456,394.
Office Action mailed Mar. 5, 2015 for U.S. Appl. No. 13/456,546.

* cited by examiner

PLASMA OR SERUM PRODUCTION AND REMOVAL OF FLUIDS UNDER REDUCED PRESSURE

RELATED APPLICATIONS

This application claims the benefit of U.S. Provisional Patent Application Ser. No. 61/480,941, filed Apr. 29, 2011, entitled "Plasma or Serum Production and Removal of Fluids under Reduced Pressure," by Haghgooie, et al.; and of U.S. Provisional Patent Application Ser. No. 61/549,437, filed Oct. 20, 2011, entitled "Systems and Methods for Collection and/or Manipulation of Blood Spots or Other Bodily Fluids," by Bernstein, et al. Each of these is incorporated herein by reference.

FIELD OF INVENTION

In some embodiments, the present invention generally relates to the separation of blood within a device to form plasma or serum. In some embodiments, the present invention generally relates to the removal of fluids, such as blood, contained within a device.

BACKGROUND

Plasma is the liquid component of blood in which blood cells are normally suspended. Serum is that portion of plasma in which clotting factors such as fibrinogens have been removed. Plasma (including serum) forms about 55% of the total volume of blood. It is mostly water (about 92-93% by volume) and contains dissolved proteins, glucose, clotting factors, mineral ions, hormones and carbon dioxide. While plasma may be prepared by spinning a tube of fresh blood containing an anti-coagulant in a centrifuge until the blood cells fall to the bottom of the tube, other techniques for producing plasma are still needed. Plasma or serum may be important, for instance, for testing or diagnostics, e.g., for infections, diabetes (e.g., sugar), AIDS (e.g., HIV), cancer (e.g., prostate-specific antigen), or other indications. In many cases, only a relatively small amount of plasma or serum is needed for testing purposes; however, a much large volume of blood is often required for centrifugation and/or processing.

SUMMARY OF THE INVENTION

In some embodiments, the present invention generally relates to the separation of blood within a device to form plasma or serum. In some embodiments, the present invention generally relates to the removal of fluids, such as blood, contained within a device. The subject matter of the present invention involves, in some cases, interrelated products, alternative solutions to a particular problem, and/or a plurality of different uses of one or more systems and/or articles.

In one aspect, the present invention is directed to a device for receiving bodily fluid from the subject and processing the bodily fluid to form plasma or serum. The device may include an inlet for introduction of a bodily fluid from the subject into the device, a separation membrane in fluid communication with the inlet on a first side of the membrane, a vacuum chamber having a pressure less than ambient pressure, and a seal that can be manipulated to control a fluid communication pathway between the vacuum chamber and a second side of the separation membrane. In another aspect, the vacuum chamber may be in gaseous communication with a second side of the membrane. In yet another aspect, the device may have an applicator region including an opening arranged to receive a fluid and a seal that can be manipulated to control a fluid communication pathway between the vacuum chamber and a second side of the separation membrane. In yet another aspect, the vacuum chamber may be in gaseous communication with a second side of the separation membrane.

In one aspect, the device may have two membranes. The first membrane separates the inlet from the storage chamber and is substantially impermeable to cells. The second membrane is gas permeable but is substantially liquid impermeable. In some embodiments, the second membrane separates the storage chamber from the vacuum chamber.

In one aspect, the device may contain an applicator region that includes an opening arranged to receive fluid from a subject.

In one aspect, the present invention is directed to a method of producing plasma or serum from blood. The method includes applying a device to the skin of a subject and causing the device to receive no more than about 5 ml of blood from the subject. The blood received from the subject is separated within the device to form plasma or serum. In another aspect, the method includes concentrating at least a portion of the blood cells in the blood received from the subject.

In one aspect, the method includes providing a device having a first chamber containing a liquid and a second chamber having a pressure less than ambient pressure. The first chamber and the second chamber are separated by a membrane. The method also includes inserting at least a portion of a needle into the first chamber, causing the needle to expel a gas into the first chamber, wherein the gas does not cause the liquid to enter the second chamber, and receiving a portion of the liquid from the first chamber into the needle.

In another aspect, the present invention encompasses methods of making one or more of the embodiments described herein, for example, a device for separating plasma or serum from blood. In still another aspect, the present invention encompasses methods of using one or more of the embodiments described herein, for example, a device for separating plasma or serum from blood.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
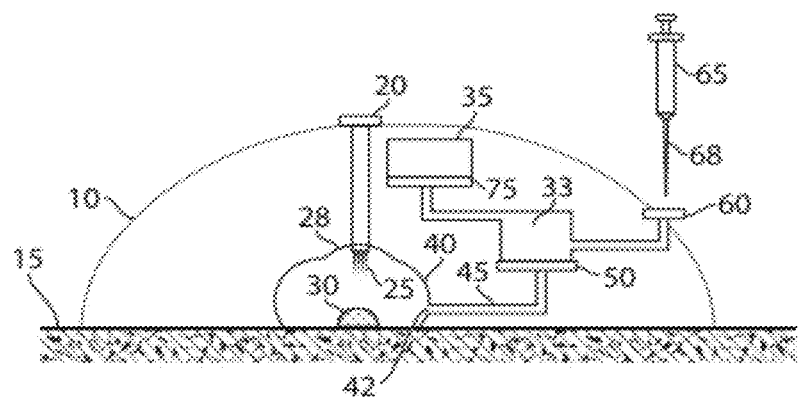
FIG. 1 illustrates a device in accordance with one embodiment of the invention, containing various membranes.

In some embodiments, the present invention generally relates to the separation of blood within a device to form plasma or serum. In some embodiments, the present invention generally relates to the removal of fluids, such as blood, contained within a device. In one aspect, the present invention is generally directed to systems and methods for receiving blood from a subject and processing the blood to form plasma or serum. For example, a device may be applied to the skin of a subject to receive blood from the subject and pass the blood through a separation membrane, which separates the blood into plasma and a portion concentrated in blood cells. As another example, blood or plasma may be allowed to clot within the device and serum (the unclotted portion of the blood) may be received from the device. The device may contain, in some cases, a vacuum source such as a pre-packaged vacuum to facilitate receiving of blood and/or passage of the blood through the separation membrane to produce plasma or serum. In certain embodiments, plasma, serum, or other fluids may be removed from the device by inserting a needle into a portion of the device that has reduced pressure, expelling gas into the device through the needle, then withdrawing plasma, serum, or other fluids through the needle. In other embodiments, the fluid within the device may be accessed without a using needle via venting manually, automatically, or by using a machine. Thereafter, fluid may be ejected, or it may be extracted using a syringe, pipette, etc.

Certain aspects of the invention are generally directed to separating blood into plasma or serum, and a portion enriched in blood cells, for example, under vacuum or reduced pressure. For example, a device, such as a portable device, may include a vacuum chamber or other vacuum source having a pressure less than atmospheric or ambient pressure. The reduced pressure may be used to draw blood (or other suitable bodily fluids) into the device and/or through a membrane, such as a separation membrane. In some embodiments, the membrane is used to separate the blood into a first portion formed of plasma or serum, and a second portion that is concentrated in blood cells.

In some cases, the device may be used to separate a relatively small amount of blood into plasma or serum and a portion concentrated in blood cells. For example, less than about 10 ml, less than about 5 ml, less than about 3 ml, less than about 2 ml, less than about 1.5 ml, less than about 1 ml, less than about 800 microliters, less than about 600 microliters, less than about 500 microliters, less than about 400 microliters, less than about 300 microliters, less than about 200 microliters, less than about 100 microliters, less than about 80 microliters, less than about 60 microliters, less than about 40 microliters, less than about 20 microliters, less than about 10 microliters, or less than about 1 microliter of blood may be received into the device and separated within the device. The plasma or serum can then be recovered from the device, for example, using a needle to remove at least a portion of the plasma or serum, and subjected to various diagnostics or testing protocols, for example, for the detection of infections, diabetes (e.g., sugar), AIDS (e.g., HIV), cancer (e.g., prostate-specific antigen), or other indications.

In some embodiments, the device may be relatively small, in contrast with machines (such as dialysis machines) that are typically used in plasmapheresis. For example, the device may be handheld or be applied to the skin of a subject, e.g., using an adhesive, as is discussed below. The device may be self-contained in some embodiments, i.e., such that the device is able to function to withdraw blood (or other bodily fluids) from a subject and separate it to produce plasma or serum without requiring external connections such as an external source of vacuum, an external source of power, or the like. For instance, a vacuum source within the device, e.g., a vacuum chamber, may be used to draw blood across the separation membrane to produce plasma or serum.

Furthermore, in certain embodiments, the device is able to effectively produce a relatively small amount of plasma or serum without requiring a relatively large amount of blood and/or without requiring a centrifuge to produce plasma or serum from the received blood. In some cases, at least about 30%, at least about 40%, at least about 50%, at least about 60%, at least about 70%, at least about 80%, or at least about 90% of the plasma or serum produced by the device may be received from the device, e.g., for use in subsequent testing or diagnostics. In contrast, in many prior art techniques where a sample of plasma or serum is required, e.g., for diagnostics or testing purposes, a relatively large volume of blood is received from a subject into a test tube (e.g., having a volume of at least 2 ml, at least 4 ml, at least 6 ml, or at least about 10 ml, such as in the Vacutainer™ (Becton, Dickinson and company) or Vacuette™ (Greiner Bio-One GmBH) systems), then the test tube is processed (for example, via centrifugation) to separate the blood from the plasma or serum. A portion of the plasma or serum is then removed from the test tube for diagnostics or testing purposes; however, the remainder of the plasma or serum within the test tube is not needed for subsequent testing or diagnostics, and is essentially wasted. Additionally, in some embodiments, serum may be produced without use of an anticoagulant within the device, although in other embodiments, the device may contain an anticoagulant to produce plasma. In some embodiments, the membrane and/or the storage chamber may contain an anticoagulant to produce plasma. Alternatively, if there is no anticoagulant present in the device, fluid that flows through a separation membrane into the storage chamber is free of blood cells and will ultimately clot in the storage chamber, thereby producing a liquid component, also known as serum. This serum can be collected via aspiration or other suitable method out of the storage chamber, leaving the blood clots in the storage chamber. Thus, many embodiments described herein may be used to produce plasma or serum, depending on the presence or absence of anticoagulant.

In some cases, the device may include a fluid transporter that receives fluid from a subject. The fluid transporter may include an applicator region where bodily fluids from the body accumulate, and a vacuum or reduced pressure may be used to withdraw the bodily fluids from the applicator region into the device, e.g., into a vacuum source or a storage chamber. In some cases, the vacuum source may be larger than the applicator region. Still other aspects of the present invention are directed to kits involving such devices, methods of making such devices, methods of using such devices, and the like.

The fluid transporter may include an opening of any size and/or geometry that is constructed to receive fluid into the device. For example, the opening may lie in a two-dimensional plane or the opening may include a three-dimensional cavity, hole, groove, slit, etc. In some embodiments, the fluid transporter may also include a flow activator, such as one or more microneedles, arranged to cause fluid to be released from the subject, e.g., by piercing the skin of a subject. In some embodiments, if fluid may partially or fully fill an enclosure surrounding a flow activator, then the enclosure can define at least part of a fluid transporter.

It should be noted that a flow activator need not be included with all embodiments as the device may not necessarily employ a mechanism for causing fluid release from the subject. For instance, the device may receive fluid that has already been released due to another cause, such as a cut or an abrasion, fluid release due to a separate and independent device, such as a separate lancet, an open fluid access such as during a surgical operation, and so on. Additionally, fluid may be introduced into the device via urination, spitting, pouring fluid into the device, etc. If included, a flow activator may physically penetrate, pierce, and/or or abrade, chemically peel, corrode and/or irritate, release and/or produce electromagnetic, acoustic or other waves, other otherwise operate to cause fluid release from a subject. The flow activator may include a moveable mechanism, e.g., to move a needle, or may not require movement to function. For example, the flow activator may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of a flow activator to cause fluid release from a subject.

One non-limiting example of such a device is now described with reference to FIG. 1; further details of this and other devices in accordance with certain aspects of the present invention are also described in further detail below. In this example, device 10 is applied to the skin 15 of a subject. The device in this figure is self-contained, i.e., such that the device is able to function to withdraw blood from a subject to produce plasma or serum without requiring external connections such as an external source of vacuum, an external source of power, or the like. In other embodiments, however, the device need not be self-contained. Upon actuation of the device shown in FIG. 1, for example, remotely or by pressing button 20, flow activators 25 are deployed into skin 15 of the subject. The flow activators may include one or more needles or microneedles, or other flow activators as discussed in detail below and/or in documents incorporated herein by reference. Copies of these documents are also included at the end of this application. As shown in this figure, the deployment of flow activators 25 into skin 15 of the subject may be accomplished using a deployment actuator 28, or by other techniques such as those described herein. The deployment actuator 28 may include suitable components to deploy the flow activators 25, such as a button, a switch, a lever, a slider, a dial, a compression spring, a Belleville spring, a servo, rotary or linear electric motor, and/or a pneumatic apparatus, or other suitable device.

A vacuum or a reduced pressure less than atmospheric or ambient pressure may be used to facilitate the movement of blood 30 into the device, as follows. The vacuum may be contained within device 10, for example, within vacuum chamber 35. Blood 30 on the skin 15 of the subject may become exposed to the vacuum or reduced pressure, which causes the blood to enter device 10, e.g., through applicator region 40 into inlet 42 of channel 45, passing through membrane 50 towards storage chamber 33. Storage chamber 33 is located immediately on the other side of membrane 50 in this particular example, and can be used to collect plasma or serum that is produced by drawing blood 30 through membrane 50. Membrane 50 may be, for example, a separation membrane or a membrane that is permeable to fluids but is substantially impermeable to cells.

When blood 30 reaches membrane 50, cells and other larger components cannot pass therethrough, while fluids and smaller components are able to pass through, thereby forming a plasma or serum within storage chamber 33 (or at least, a plasma-enriched fluid). Plasma or serum present within storage chamber 33 may be collected, e.g., for subsequent use and/or analysis. In contrast, other components on the other side of membrane 50 may remain there, thereby forming a portion that is concentrated or enriched in blood cells, i.e., the concentration of blood cells in this portion may be higher than the initial concentration of blood cells in the blood received from the subject.

In some embodiments, blood spots may be produced on a blood spot membrane. In these cases, channel 45 may have a small volume relative to the volume of a blood spot membrane which may be very porous and may collect fluid. The blood spot membrane is used to collect fluid. The blood spot membrane is not used to separate cells/plasma (as opposed to the separation membranes discussed earlier). Fluid may fill the blood spot membrane. A second hydrophobic membrane may be positioned on top of the collection membrane. Once fluid contacts the hydrophobic membrane, fluid collection ceases. The blood spot membrane may remain in the device to dry and is then removed from the device. Alternatively, the blood spot membrane may be removed from the device and dried outside of the device. In either case, vacuum is released prior to removal of the blood spot membrane.

The plasma or serum may be removed from storage chamber 33 using any suitable technique. One non-limiting example is now described. However, it should be understood that other techniques may be used instead of and/or in addition to the following, and that this technique may also be applied to remove blood (or other bodily fluids) from a device such as device 10, whether separation of the blood into plasma or serum has occurred or not. Examples of other suitable techniques are disclosed in U.S. patent application Ser. No. 13/006,165, filed Jan. 13, 2011, entitled "Sampling Device Interfaces," by Chickering, et al., incorporated herein by reference in its entirety.

As one example, in certain cases, syringe 65 may be introduced through septum 60 to reach the storage chamber and/or a portion of the device that is in fluidic communication with storage chamber 33. However, syringe 65 may contain air, typically at atmospheric or ambient pressure, e.g., within needle 68 of syringe 65. Upon entry of needle 68 through septum 60 such that needle 68 becomes fluidly communicative with storage chamber 33 (which is typically at a vacuum or reduced pressure, as previously described), the air may cause the plasma, serum, or other liquids to be moved or "blown" around the device, especially within storage chamber 33, and in some cases in a relatively uncontrolled fashion. In certain embodiments, to mitigate or reduce the effects of the introduction of additional air into storage chamber 33, vacuum chamber 35 may be separated from storage chamber 33 so that additional air can be introduced into device 10 without causing the plasma, serum, or other liquids within storage chamber 33 to be moved around within the device, e.g., exiting storage chamber 33. As a non-limiting example, as shown in FIG. 1, a second membrane 75 separates vacuum chamber 35 from storage chamber 33. Second membrane 75 may be selected so as to allow passage of gases but prevent the passage of liquids. For example, second membrane 75 can be a relatively hydrophobic membrane, or a membrane that has a contact angle of at least 45° relative to an air/water interface. Other suitable membranes are discussed below. Accordingly, when air is introduced into storage chamber 33, some of the air may pass across second membrane 75 into vacuum chamber 35; however, a liquid such as plasma, serum, or blood within storage chamber 33 is unable to pass into vacuum chamber 35, even under the influence of a driving force caused by the introduction of air into storage chamber 33, and thus the liquid remains within storage chamber 33 after the pressures within device 10 and needle 68, and/or the pressures within storage chamber 33 and vacuum chamber 35 have substantially equalized.

Accordingly, in certain aspects, the present invention is generally directed to devices able to withdraw or extracting blood, interstitial fluid, or other bodily fluids from the skin of a subject, e.g., from the skin and/or from beneath the skin, or other mucosal surface, as well as methods of use thereof. The received fluid may be any suitable bodily fluid, such as interstitial fluid, other skin-associated material, mucosal material or fluid, whole blood, perspiration, saliva, plasma, serum, tears, lymph, urine, or any other bodily fluid, or combinations thereof. Substances received from a subject can include solid or semi-solid material such as skin, cells, or any other substance from the skin and/or beneath the skin of the subject. Substances that can be delivered to a subject in accordance with some embodiments of the invention include diagnostic substances, therapeutic substances such as drugs, and the like. Various embodiments of the invention are described below in the context of delivering or receiving a fluid, such as blood or interstitial fluid, from the skin and/or beneath the skin. It is to be understood that in all embodiments herein, regardless of the specific exemplary language used (e.g., withdrawing blood), the devices and methods of other embodiments of the invention can be used for receiving any substance from the skin and/or from beneath the skin of the subject, and/or for delivering any substance to the subject, e.g., to the skin and/or a location beneath the skin of the subject.

In some cases, the device may contain a flow activator (for example, one or more needles or microneedles). Examples of flow activators are discussed in detail below. In some cases, the device may be used to pierce the skin of the subject, and fluid can then be delivered to and/or received from the skin of the subject. Thus, it should be understood that in the discussions herein, references to withdrawing a fluid "from the skin" includes embodiments in which a fluid is delivered and/or received through the surface of the skin. For example, a fluid may be delivered into or received from a layer of skin in one embodiment, while in another embodiment a fluid may be delivered into or received from a region just below the skin of the subject, e.g., passing through the surface of the skin, as opposed to other routes of administration such as oral delivery. The subject is usually human, although non-human subjects may be used in certain instances, for instance, other mammals such as a dog, a cat, a horse, a rabbit, a cow, a pig, a sheep, a goat, a rat (e.g., *Rattus norvegicus*), a mouse (e.g., *Mus musculus*), a guinea pig, a hamster, a primate (e.g., a monkey, a chimpanzee, a baboon, an ape, a gorilla, etc.), or the like.

As mentioned, in one aspect, blood received from a subject into a device may be separated within the device to form plasma or serum by passing the blood, or at least a portion thereof, through a separation membrane or a membrane that is permeable to fluids but is substantially impermeable to cells. The separation membrane can be any membrane able to separate blood passing therethrough into a first portion (passing through the membrane) that is enriched in plasma or serum, and a second portion (rejected by the membrane) concentrated in blood cells. In some cases, the separation membrane may have a separation effectiveness during use (the separation effectiveness is the volume of plasma or serum that passes through the membrane relative to the starting volume of whole blood) of at least about 5%, at least about 10%, at least about 20%, at least about 40%, at least about 50%, at least about 55%, or at least about 60%.

In one set of embodiments, the separation membrane is selected to have a pore size smaller than the average or effective diameter of blood cells contained within the blood, including red blood cells and white blood cells. For instance, the pore size of the separation membrane may be less than about 30 micrometers, less than about 20 micrometers, less than about 10 micrometers, less than about 8 micrometers, less than about 6 micrometers, less than about 4 micrometers, less than about 3 micrometers, less than about 2 micrometers, less than about 1.5 micrometers, less than about 1 micrometer, less than about 0.5 micrometers, etc. As specific non-limiting examples, the pore size may be between about 0.5 micrometers and about 2 micrometers, or between about 0.5 micrometers and about 1 micrometer. In addition, in some embodiments, the separation membrane may have a thickness of less than about 1 mm, less than about 750 micrometers, less than about 500 micrometers, less than about 400 micrometers, less than about 350 micrometers, less than about 300 micrometers, less than about 250 micrometers, or less than about 200 micrometers.

The separation membrane may be formed out of any suitable material. For example, in some embodiments, the separation membrane may be formed out of a material that promotes thrombolysis or inhibits clot formation, such as a polyester, and/or the separation membrane may be formed and/or coated with a biocompatible material, or at least a material that does not cause an active clotting response within the blood that the separation membrane is exposed to. As specific non-limiting example, the separation membrane can comprise or be formed from glass (e.g., glass fibers), and/or a polymer such as a polycarbonate, a polysulfone, a polyethersulfone, a polyarylethersulfone, a polyvinylpyrrolidone, a polypropylene, poly(2-methoxyethylacrylate), and/or a nitrocellulose, etc. In some embodiments, the membrane may include a copolymer such as a graft copolymer (for example, poly(propylene-graft-2-methoxyethylacrylate)), e.g., including any one or more of these polymers and/or other suitable polymers. In some cases, the separation membrane may be asymmetric, e.g., having a different separation effectiveness depending on which way blood is passed across the separation membrane to produce plasma. Many such separation membranes may be readily obtained commercially, such as Pall Vivid Plasma Separation Membrane (GF, GX, and GR), as well as other commercially available separation membranes.

During use, blood is moved towards the separation membrane using a suitable driving force to move the blood, for example, vacuum or other reduced pressure as is discussed herein. A fluidic portion of the blood is able to pass across the separation membrane to form plasma or serum on one side of the membrane, while other portions of the blood, e.g., red and white blood cells, are rejected by the membrane and thus form a portion that becomes concentrated in blood cells. For example, serum may be produced if no anticoagulant is present, in accordance with certain embodiments. Either or both portions of the blood may be collected, e.g., in an appropriate storage chamber, for further use, analysis, storage, etc., as is discussed herein.

As mentioned, in certain aspects, blood may be drawn from a subject through an applicator region in the device. The applicator region may be positioned to collect a bodily fluid on the skin of the subject that is released by a flow activator. Non-limiting examples of bodily fluids include blood or interstitial fluid, as is discussed herein. The flow activator may be applied to the skin, and optionally received from the skin, in order to cause the release of a bodily fluid to the applicator region of the device. For example, a flow activator may include one or more needles or microneedles, a hygroscopic agent, etc., as is discussed herein. The flow activator can be centered with respect to the applicator region in certain embodiments; in other embodiments, however, the flow activator is not centered within the applicator region, and in some embodiments, the flow activator may not necessarily enter the applicator region. The applicator region may be any portion of the device that is sized and/or positioned to collect bodily fluids, and in some cases, the applicator region may have a relatively small size and/or volume.

In one set of embodiments, the volume of the applicator region is defined relative to the opening of the applicator region, or the portion of the applicator region that is adjacent the skin of the subject when the device is applied to the skin of the subject. In some embodiments, the applicator region may be a recess or an indentation within the base of the device, which can receive a fluid from the surface of the skin. The applicator region may have any suitable shape. For example, the applicator region can be generally hemispherical, semi-oval, rectangular, irregular, etc. The volume of the applicator region can be relatively small in some embodiments. For example, the volume of the applicator region may be less than about 10 ml, less than about 8 ml, less than about 5 ml, less than about 3 ml, less than about 2 ml, less than about 1.5 ml, less than about 1 ml, less than about 800 microliters, less than about 600 microliters, less than about 500 microliters, less than about 400 microliters, less than about 300 microliters, less than about 200 microliters, or less than about 100 microliters. Smaller volumes may be desirable, for example, to minimize the amount of bodily fluid collected within the applicator region before the bodily fluid is able to be transported into the device, e.g., through an inlet within the applicator region into the device.

In some instances, the applicator region may have a small volume relative to a vacuum chamber contained within the device, e.g., in embodiments where a vacuum chamber is present in the device. The vacuum chamber may be a prepackaged vacuum chamber as is discussed below. Without wishing to be bound by any theory, it is believed that a relatively small applicator region will result in less gas being drawn into the vacuum chamber upon the creation of a fluid communication pathway between the vacuum source and the applicator region, e.g., as is discussed herein. This may allow more of the vacuum or reduced pressure to be able to draw more bodily fluid into the device. Thus, for example, the ratio between the volume of the applicator region to the volume of the vacuum chamber can be at least about 1:5, at least about 1:8, at least about 1:10, at least about 1:12, at least about 1:15, etc.

The applicator region may also contain one or more inlets for introduction of a bodily fluid from the subject into the device. For example, the inlet can be an inlet to a fluid communication pathway, a channel such as a microfluidic channel, or the like, which may extend to the separation membrane, and/or to other portions of the device, e.g., such that fluids entering the inlet are able to reach the separation membrane, for example, under action of vacuum or reduced pressure being used to move the fluid towards the separation membrane. See also U.S. Provisional Patent Application Ser. No. 61/480,977, entitled "Delivering and/or Receiving Fluids," by Gonzales-Zugasti, et al., filed on Apr. 29, 2011, incorporated herein by reference in its entirety. Thus, the fluid communication pathway into the device may proceed to, for example, a vacuum chamber, a storage or collection chamber, a separation membrane, a portion of the device containing a sensor, or the like, and/or one or more of these. In some cases, a seal can be manipulated to control the fluid communication pathway. In some cases, the seal may be manipulated reversibly to open and close the fluid communication pathway. For example, the seal may be a valve that can be opened and closed manually, automatically, with a machine, etc. The seal may also be manipulated irreversibly. For example, the seal may be punctured to open the fluid communication pathway and unable to re-seal. As non-limiting examples, the fluid communication pathway may include one or more microfluidic channels as discussed herein; for example, the fluid communication pathway may include one or more microfluidic channels having an average cross-sectional diameter of between about 100 and about 700 micrometers, or between about 300 and about 500 micrometers. Other examples of fluid communication pathways are discussed herein, including other channels and microfluidic channels.

The inlet may be positioned in any suitable location within the applicator region, and one or more inlets may be present. In some cases, an inlet (or at least a portion thereof) may be positioned relatively close to the skin of the subject. For example, the inlet may be positioned such that at least a portion of the inlet is positioned within about 5 micrometers, within about 3 micrometers, within about 1 micrometer, within about 0.7 micrometers, within about 0.5 micrometers, or within about 0.3 micrometers of the skin or the opening of the applicator region. As additional examples, the inlet (or at least a portion thereof) may be positioned to be within about 50%, within about 30%, within about 20%, within about 10%, or within about 5% of the skin of the subject or the opening of the applicator region, where the percentage may be taken relative to the distance between the opening of the applicator region and a point within the applicator region perpendicularly furthest away from the opening.

In some aspects, a seal or other suitable apparatus may be used to control a fluid communication pathway, for example, between the inlet and a vacuum chamber and/or a storage chamber. For example, the seal may comprise a valve or a pierceable surface that can be opened. However, enabling fluid communication between a vacuum source and a fluid transporter opening need not necessarily involve the opening of a valve or other device that blocks flow, but instead may involve the creation of suitable vacuum to cause flow. In some embodiments, the seal is reversible, i.e., the seal may also be used to end the fluid communication pathway (for example, a valve that can be opened or closed). In other embodiments, however, the seal is not reversible. The seal can be activated using any suitable technique, e.g., automatically, remotely, manually, etc. In some cases, the seal may be self-activating, e.g., upon application to the skin of a subject. The seal may be activated once, or multiple times in some cases. The seal may be activated, for example, by pushing a button, flipping a switch, moving a slider, turning a dial, or the like. The subject, and/or another person, may activate the seal. In some embodiments, the seal, or at least a portion thereof, may also serve as an activator, as discussed herein. Other examples of seals are discussed U.S. Provisional Patent Application Ser. No. 61/480,977, entitled "Delivering and/or Receiving Fluids," by Gonzales-Zugasti, et al., filed on Apr. 29, 2011, incorporated herein by reference in its entirety.

Thus, according to certain aspects of the invention, a vacuum (or reduced pressure) may be used to facilitate the withdraw of blood (or other bodily fluids) from the subject, and/or for causing the blood received from the subject to be separated within the device to form plasma or serum, and a portion concentrated in blood cells. Accordingly, in some aspects, the device may contain a suitable vacuum source. In some cases, the vacuum source is one that is self-contained within the device, i.e., the device need not be connected to an external vacuum source (e.g., a house vacuum) during use of the device to withdraw blood, interstitial fluid, or other bodily fluids from the skin and/or from beneath the skin. In certain embodiments, relatively small vacuum chambers may be used, e.g., so that the device may have a relatively small size. For example, the vacuum chamber may have a volume of less than about 25 ml, less than about 20 ml, less than about 15 ml, less than about 10 ml, less than about 5 ml, less than about 3 ml, less than about 2 ml, or less than about 1 ml.

For example, in one set of embodiments, the vacuum source may include a vacuum chamber having a pressure less than atmospheric or ambient pressure before blood (or other fluid) is received into the device, i.e., the vacuum chamber is at a "negative pressure" (that is, negative relative to atmospheric or ambient pressure) or a "vacuum pressure" (or just having a "vacuum"). For example, the vacuum in the vacuum chamber may be at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least 650 mmHg, at least about 700 mmHg, or at least about 750 mmHg, i.e., below atmospheric or ambient pressure. Thus, the pressure within the vacuum is at a "reduced pressure" relative to atmospheric or ambient pressure, e.g., the vacuum chamber is a reduced pressure chamber. However, in other embodiments, it should be understood that other pressures may be used and/or that different methods may be used to produce other pressures (greater than or less than atmospheric or ambient pressure). As non-limiting examples, an external vacuum or a mechanical device may be used as the vacuum source; various additional examples are discussed in detail herein.

As mentioned, the vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least about 600 mmHg, at least 650 mmHg, at least about 700 mmHg, or at least about 750 mmHg may be applied to the skin. As used herein, "vacuum" refers to pressures that are below atmospheric or ambient pressure.

Any source of vacuum may be used. For example, the device may comprise an internal vacuum source, and/or be connectable to a vacuum source is external to the device, such as a vacuum pump or an external (line) vacuum source. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like.

As a specific, non-limiting example, in one embodiment, a device may be used to withdraw fluid using a vacuum without an external power and/or a vacuum source. Examples of such devices that can use vacuum include skin patches, strips, tapes, bandages, or the like. For instance, a skin patch may be contacted with the skin of a subject, and a vacuum created through a change in shape of a portion of the skin patch or other device (e.g., using a shape memory polymer), which may be used to deliver to and/or withdraw fluid from the skin and/or beneath the skin. As a specific example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As another example, a mechanical device may be used to create the vacuum, For example, springs, coils, expanding foam (e.g., from a compressed state), a shape memory polymer, shape memory metal, or the like may be stored in a compressed or wound state upon application to a subject, then released (e.g., unwinding, uncompressing, etc.), to mechanically create the vacuum. In some embodiments, the device may be used to create a vacuum automatically, once activated, without any external control by a user.

Thus, in some cases, the device is "pre-packaged" with a suitable vacuum source (e.g., a pre-evacuated vacuum chamber); for instance, in one embodiment, the device may be applied to the skin and activated in some fashion to create and/or access the vacuum source. In yet another example, a chemical reaction may be used to create a vacuum, e.g., a reaction in which a gas is produced, which can be harnessed to provide the mechanical force to create a vacuum. In still another example, a component of the device may be able to create a vacuum in the absence of mechanical force. In another example, the device may include a self-contained vacuum actuator, for example, chemical reactants, a deformable structure, a spring, a piston, etc.

In one set of embodiments, the device may be able to create a pressure differential (e.g. a vacuum). For example, the device may contain a pressure differential chamber, such as a vacuum chamber or a pressurized chamber, that can be used to create a pressure differential. The pressure differential may be created by a pressure regulator. As used here, "pressure regulator" is a pressure controller component or system able to create a pressure differential between two or more locations. The pressure differential should be at least sufficient to urge or move fluid or other material in accordance with various embodiments of the invention as discussed herein, and the absolute pressures at the two or more locations are not important so long as their differential is appropriate, and their absolute values are reasonable for the purposes discussed herein. For example, the pressure regulator may produce a pressure higher than atmospheric or ambient pressure in one location, relative to a lower pressure at another location (atmospheric or ambient pressure or some other pressure), where the differential between the pressures is sufficient to urge or move fluid in accordance with the invention. In another example, the regulator or controller will involve a pressure lower than atmospheric or ambient pressure (a vacuum) in one location, and a higher pressure at another location(s) (atmospheric or ambient pressure or a different pressure) where the differential between the pressures is sufficient to urge or move fluid in accordance with the invention. Wherever "vacuum" or "pressure" is used herein, it should be understood that the opposite can be implemented as well, as would be understood by those of ordinary skill in the art, i.e., a vacuum chamber can be replaced in many instances with a pressure chamber, for creating a pressure differential suitable for urging the movement of fluid or other material.

The pressure regulator may be an external source of vacuum (e.g. a lab, clinic, hospital, etc., house vacuum line or external vacuum pump), a mechanical device, a vacuum chamber, pre-packaged vacuum chamber, a pressurized chamber, or the like. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like. Vacuum chambers can be used in some embodiments, where the device contains, e.g., regions in which a vacuum exits or can be created (e.g. a variable volume chamber, a change in volume of which will affect vacuum or pressure). A vacuum chamber can include pre-evacuated (i.e., pre-packaged) chambers or regions, and/or self-contained actuators.

A "self-contained" vacuum (or pressure) regulator means one that is associated with (e.g., on or within) the device, e.g. one that defines an integral part of the device, or is a separate component constructed and arranged to be specifically connectable to the particular device to form a pressure differential (i.e., not a connection to an external source of vacuum such as a hospital's, clinic's, or lab's house vacuum line, or a vacuum pump suitable for general use). In some embodiments, the self-contained vacuum source may be actuated in some fashion to create a vacuum within the device. For instance, the self-contained vacuum source may include a piston, a syringe, a mechanical device such as a vacuum pump able to create a vacuum within the device, and/or chemicals or other reactants that can react to increase or decrease pressure which, with the assistance of mechanical or other means driven by the reaction, can form a pressure differential associated with a pressure regulator. Chemical reaction can also drive mechanical actuation with or without a change in pressure based on the chemical reaction itself. A self-contained vacuum source can also include an expandable foam, a shape memory material, or the like.

One category of self-contained vacuum or pressure regulators of the invention includes self-contained assisted regulators. These are regulators that, upon actuation (e.g., the push of a button, or automatic actuation upon, e.g., removal from a package or urging a device against the skin), a vacuum or pressure associated with the device is formed where the force that pressurizes or evacuates a chamber is not the same as the actuation force. Examples of self-contained assisted regulators include chambers evacuated by expansion driven by a spring triggered by actuation, release of a shape-memory material or expandable material upon actuation, initiation of a chemical reaction upon actuation, or the like.

Another category of self-contained vacuum or pressure regulators of the invention are devices that are not necessarily pre-packaged with pressure or vacuum, but which can be pressurized or evacuated, e.g. by a subject, health care professional at a hospital or clinic prior to use, e.g. by connecting a chamber of the device to a source of vacuum or pressure. For example, the subject, or another person, may actuate the device to create a pressure or vacuum within the device, for example, immediately prior to use of the device.

The vacuum or pressure regulator may be a "pre-packaged" pressure or vacuum chamber in the device when used (i.e., the device can be provided ready for use by a subject or practitioner with an evacuated region on or in the device, without the need for any actuation to form the initial vacuum). A pre-packaged pressure or vacuum chamber regulator can, e.g., be a region evacuated (relative to atmospheric or ambient pressure) upon manufacture and/or at some point prior to the point at which it is used by a subject or practitioner. For example, a chamber is evacuated upon manufacture, or after manufacture but before delivery of the device to the user, e.g. the clinician or subject. For instance, in some embodiments, the device contains a vacuum chamber having a vacuum of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least about 550 mmHg, at least about 600 mmHg, at least about 650 mmHg, at least about 700 mmHg, or at least about 750 mmHg below atmospheric or ambient pressure.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum chamber may be in fluidic communication with one or more needles, and the reduced pressure can be used to move the skin towards the device, withdraw fluid from the skin and/or beneath the skin, or the like.

As another example, a shape memory polymer may be shaped to be flat at a first temperature (e.g., room temperature) but curved at a second temperature (e.g., body temperature), and when applied to the skin, the shape memory polymer may alter from a flat shape to a curved shape, thereby creating a vacuum. As yet another example, a mechanical device may be used to create the vacuum, For example, springs, coils, expanding foam (e.g., from a compressed state), a shape memory polymer, shape memory metal, or the like may be stored in a compressed or wound released upon application to a subject, then released (e.g., unwinding, uncompressing, etc.), to mechanically create the vacuum. Non-limiting examples of shape-memory polymers and metals include Nitinol, compositions of oligo(epsilon-caprolactone)diol and crystallizable oligo(rho-dioxanone)diol, or compositions of oligo(epsilon-caprolactone)dimethacrylate and n-butyl acrylate.

In yet another example, a chemical reaction may be used to create a vacuum, e.g., a reaction in which a gas is produced, which can be harnessed to provide the mechanical force to create a vacuum. In some embodiments, the device may be used to create a vacuum automatically, once activated, without any external control by a user.

Figure 3:
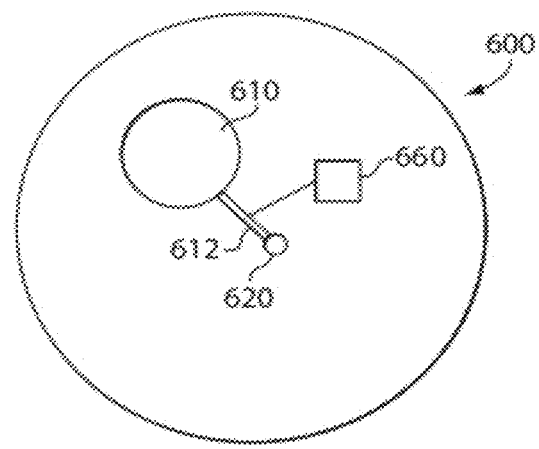
FIG. 3 illustrates a device in one embodiment of the invention, having a vacuum chamber.

In one set of embodiments, the device contains a vacuum chamber that is also used as a storage chamber to receive blood, interstitial fluid, or other fluid received from the skin and/or beneath the skin of the subject into the device. For instance, blood received from a subject through or via the fluid transporter may enter the vacuum chamber due to its negative pressure (i.e., because the chamber has an internal pressure less than atmospheric or ambient pressure) to produce plasma or serum, and the blood, serum and/or plasma may be optionally stored in the device, e.g., within a storage or collection chamber, or within a vacuum chamber for later use. A non-limiting example is illustrated in FIG. 3. In this figure, device 600 contains vacuum chamber 610, which is connected to flow activator 620 (which may be, e.g., one or more needles or microneedles). Upon activation of vacuum chamber 610 (e.g., using actuator 660, as discussed herein), vacuum chamber 610 may be put into fluidic communication with flow activator 620. Flow activator 620 may accordingly cause negative pressure to be applied to the skin of the subject, for instance, due to the internal pressure within vacuum chamber 610. Blood received from the skin and/or beneath the skin via flow activator 620 may accordingly be drawn into the device and into vacuum chamber 610, e.g., through conduit 612. Upon entry into the device, the blood may be passed across a separation membrane or a membrane that is permeable to fluids but is substantially impermeable to cells.

In another set of embodiments, however, the device may include separate vacuum chambers and storage chambers (e.g., chambers to store fluid such as blood, serum, or plasma from the skin and/or beneath the skin of the subject). The vacuum chamber and storage chambers may be in fluid communication, and may have any suitable arrangement. In some embodiments, the vacuum from the vacuum chamber may be used, at least in part, to withdraw fluid from the skin and/or beneath the skin, which is then directed into a storage chamber, e.g., for later analysis or use, for example, as discussed below. As an example, blood may be received into the device, flowing towards a vacuum chamber, but the blood (or other fluid) may be prevented from entering the vacuum chamber. For instance, in certain embodiments, a material permeable to gas but not to a liquid such as blood or interstitial fluid may be used. For example, the material may be a membrane such as a hydrophilic or hydrophobic membrane having a suitable porosity, a porous structure, a porous ceramic frit, a dissolvable interface (e.g., formed from a salt or a polymer, etc.), or the like.

Figure 4:
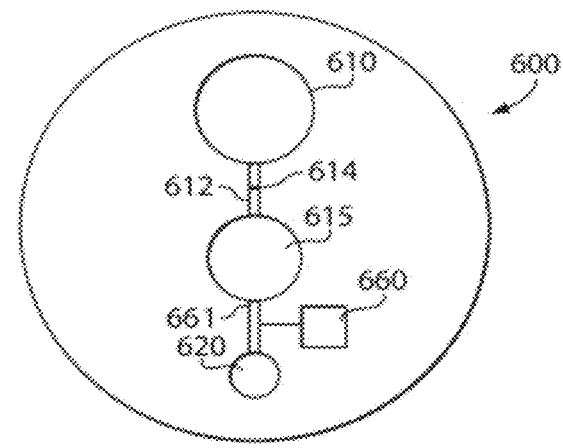
FIG. 4 illustrates a device in another embodiment of the invention, having a vacuum chamber and a storage chamber.

One non-limiting example is illustrated in FIG. 4. In this figure, device 600 contains vacuum chamber 610 and storage chamber 615. Vacuum chamber 610 can be put in fluidic communication with storage chamber 615 via conduit 612, which contains material 614. Material 614 may be any material permeable to gas but not to a liquid in this example, e.g., material 614 may be a membrane such as a hydrophilic membrane or a hydrophobic membrane that has a porosity that allows gas exchange to occur but does not allow the passage of blood or interstitial fluid from the skin and/or beneath the skin of the subject. When device 600 is actuated using actuator 660, blood (or other fluid) flows through flow activator 620 via conduit 661 into storage chamber 615 because of the internal vacuum pressure from vacuum chamber 610, which is not completely impeded by material 614 since it is permeable to gases. However, because of material 614, blood (or other bodily fluid) is prevented from entering vacuum chamber 610, and instead remains in storage chamber 615, e.g., for later analysis or use.

The needle (or other flow activator) may be used for delivering to and/or receiving fluids or other materials from a subject, e.g., to or from the skin and/or beneath the skin. For example, in some cases, a vacuum chamber having a reduced pressure or an internal pressure less than atmospheric or ambient pressure prior to receiving blood or other bodily fluids (e.g., interstitial fluid) may be used to assist in the receiving of the fluid from the skin after the needle (or other flow activator) has penetrated the skin. The fluid received from the skin and/or beneath the skin may be collected in the vacuum chamber and/or in a storage chamber. The storage chamber may be separated from the vacuum chamber using a gas permeable membrane (e.g., one that is substantially impermeable to blood or other bodily fluids), a hydrophobic membrane, a hydrophilic membrane, a porous structure, a dissolvable interface, or the like, e.g., as is discussed herein.

In some embodiments, the flow of blood (or other fluid, e.g., interstitial fluid) into the storage chamber may be controlled using a flow controller. The flow controller may be manually and/or automatically controlled to control the flow of blood. The flow controller may activate or deactivate when a certain amount or volume of fluid has entered the storage chamber in certain cases. For instance, the flow controller may stop blood flow after a predetermined amount or volume of blood has entered the storage chamber, and/or the flow controller may be able to control the internal pressure of the storage chamber, e.g., to a specific level, such as a predetermined level. Examples of suitable flow controllers for the device include, but are not limited to, a membrane, a valve, a dissolvable interface, a gate, or the like.

Figure 5:
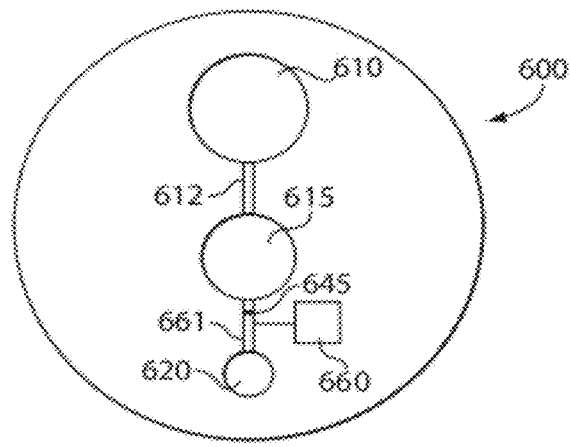
FIG. 5 illustrates a device in yet another embodiment of the invention, having a flow controller.

One non-limiting example of a flow controller is now illustrated with reference to FIG. 5. In this example figure, device 600 includes a vacuum chamber 610 and a storage chamber 615. Fluid entering device 600 via flow activator 620 is prevented from entering storage chamber 615 due to flow controller 645 present within conduit 611. However, under suitable conditions, flow controller 645 may be opened, thereby allowing at least some fluid to enter storage chamber 615. In some cases, for instance, storage chamber 615 also contains at least a partial vacuum, although this vacuum may be greater or less than the pressure within chamber 610. In other embodiments, flow controller 645 may initially be open, or be externally controllable (e.g., via an actuator), or the like. In some cases, the flow controller may control the flow of fluid into the device such that, after collection, at least some vacuum is still present in the device.

Thus, in some cases, the device may be constructed and arranged to reproducibly obtain from the skin and/or from beneath the skin of the subject a controlled amount of fluid, e.g., a controlled amount or volume of blood or interstitial fluid. The amount of fluid reproducibly obtained from the skin and/or beneath the skin of the subject may be controlled, for example, using flow controllers, materials permeable to gas but not to liquids, membranes, valves, pumps, gates, microfluidic systems, or the like, as discussed herein. In particular, it should be noted that the volume of blood or other fluid obtained from the skin and/or beneath the skin of the subject need not be strictly a function of the initial vacuum pressure or volume within the device. For example, a flow controller may initially be opened (e.g., manually, automatically, electronically, etc.) to allow fluid to begin entering the device; and when a predetermined condition is reached (e.g., when a certain volume or amount of blood or interstitial fluid has entered the device), the flow controller may be closed at that point, even if some vacuum remains within the device. In some cases, this control of fluid allows the amount of fluid reproducibly obtained from the skin and/or beneath the skin of the subject to be controlled to a great extent. For example, in one set of embodiments, the amount of fluid received from the skin and/or beneath the skin of the subject may be controlled to be less than about 1 ml, may be less than about 300 microliters, less than about 200 microliters, less than about 100 microliters, less than about 50 microliters, less than about 30 microliters, less than about 20 microliters, less than about 10 microliters, less than about 5 microliters, less than about 3 microliters, less than about 2 microliters, less than about 1 microliter, etc.

Figure 6:
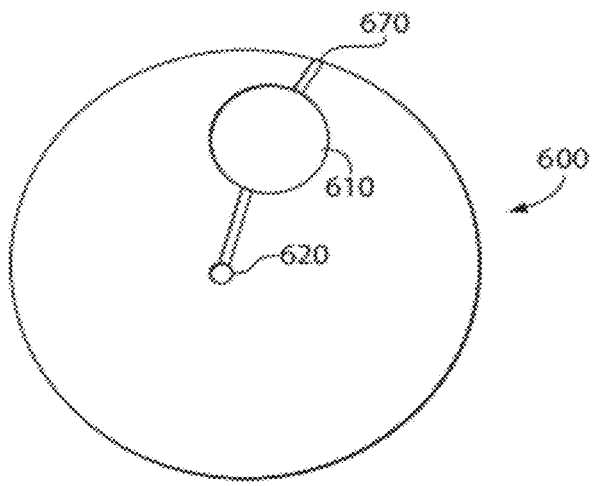
FIG. 6 illustrates a device according to another embodiment of the invention.

In some embodiments, the device may be connected to an external apparatus for determining at least a portion of the device, a fluid (e.g., plasma or serum) removed from the device, an analyte suspected of being present within the fluid, or the like. For example, the device may be connected to an external analytical apparatus, and fluid removed from the device for later analysis, or the fluid may be analyzed within the device in situ, e.g., by adding one or more reaction entities to the device, for instance, to a storage chamber, or to analytical chamber within the device. For example, in one embodiment, the external apparatus may have a port or other suitable surface for mating with a port or other suitable surface on the device, and blood, interstitial fluid, or other fluid can be removed from the device using any suitable technique, e.g., using vacuum or pressure, etc. The blood or other fluid may be removed by the external apparatus, and optionally, stored and/or analyzed in some fashion. For example, in one set of embodiments, the device may include an exit port for removing a fluid from the device (e.g., blood). In some embodiments, fluid contained within a storage chamber in the device may be removed from the device, and stored for later use or analyzed outside of the device. In some cases, the exit port may be separate from the flow activator. An example is shown with exit port 670 and flow activator 620 in device 600 in FIG. 6. As shown in this figure, the exit port can be in fluidic communication with vacuum chamber 610. As another example, an exit port can be in fluidic communication with a vacuum chamber, which can also serve as a fluid reservoir in some cases. Other methods for removing blood, interstitial fluid, or other fluids from the device include, but are not limited to, removal using a vacuum line, a pipette, extraction through a septum instead of an exit port, or the like. In some cases, the device may also be positioned in a centrifuge and subjected to various g forces (e.g., to a centripetal force of at least 50 g), e.g., to cause at separation of cells or other substances within a fluid within the device to occur.

One aspect of the invention is generally directed to methods for withdrawing liquid from a device. The liquid may be blood, plasma, serum, or other fluids contained within the device. For example, in one set of embodiments, a liquid such as plasma or serum may be removed from a storage chamber within the device. The storage chamber may also be a vacuum chamber, or the storage chamber may be one that is at least partially separated from a vacuum chamber, for example, by a membrane. In addition, in some cases, a seal can be used to control a fluid communication pathway between the vacuum chamber and the storage chamber. In one set of embodiments, a storage chamber containing a fluid such as plasma or serum can be in gaseous communication with the vacuum chamber, e.g., such that the pressures within the storage chamber and the vacuum chamber are substantially equal. However, the storage chamber and the vacuum chamber may not necessarily be in liquid communication with each other, for example, due to the presence of a membrane or other structure (e.g., a retaining wall) separating the storage chamber and the vacuum chamber. If a membrane is used, the membrane can be, for example, a hydrophobic membrane, or a membrane that is gas permeable but is substantially liquid impermeable.

To remove a fluid such as plasma or serum from the storage chamber, a needle (e.g., of a syringe) may be inserted through a septum or other pierceable material into the storage chamber, and/or to a portion of the device in fluidic communication with the storage chamber, e.g., such that the needle can access a liquid within the storage chamber or in fluidic communication with the storage chamber. The needle may be inserted, e.g., manually or automatically by an external apparatus, e.g., as is described herein. The septum or other pierceable material may comprise, for example, silicone or another suitable material, and in some cases, can be re-sealed once the needle has been removed, e.g., to maintain the pressure within the device at a vacuum or reduced pressure.

However, the needle can contain some residual gas (typically air). Thus, upon insertion of the needle into the device, the gas from within the needle may be introduced into the device, e.g., into the storage chamber. In some cases, the pressure of the gas within the needle is greater than the pressure within the storage chamber, and the difference in pressure and the introduction of gas from the needle into the storage chamber may cause liquids within the storage chamber to move within the device. In some cases, the movement or flow of the liquids may be relatively uncontrolled within the device as the pressures within the device re-equalize due to the presence of the needle and the gases contained therein.

Accordingly, in certain embodiments of the invention, one or more membranes may be used to at least partially confine liquids within the storage chamber such that the liquids do not move around the device, and/or are permitted to only move around certain portions of the device, while gases may be permitted to move within the device, e.g., to substantially equalize pressures within the device. For example, one or more membranes or other suitable structures may be used to contain a liquid, such as plasma or serum, within the storage chamber.

If membranes are used, the membranes may be selected, for example, to be substantially hydrophobic, and/or such that the membrane is gas permeable but is substantially liquid impermeable. For example, the membrane may be selected to have a pore size that allows gaseous exchange to occur but is too small to allow substantial liquid penetration to occur (e.g., due to capillary action). For example, the membrane may have a pore size of less than about 1000 micrometers, less than about 500 micrometers, less than about 300 micrometers, less than about 100 micrometers, less than about 50 micrometers, less than about 30 micrometers, less than about 10 micrometers, less than about 5 micrometers, less than about 3 micrometers, or less than about 1 micrometer. In some embodiments, the membrane may be chosen to be substantially hydrophobic, e.g., if the liquid contained within the storage chamber is aqueous or hydrophilic. For example, the hydrophobic membrane may exhibit a water/air contact angle of at least about 45° or at least about 90°.

The membrane may be formed out of any suitable material. For example, the membrane may include a polymer such as a copolymer. In some embodiments, the membrane may include one or more polymers such as a polyamide, a polypropylene, a polyvinyl chloride, a polyvinylacetate, a nylon, a polyvinylidene fluoride (PVDF), a polytetrafluoroethylene (PTFE), acrylic, unsaturated polyester (UPE), or the like. Many such polymeric membranes may be readily obtained commercially, such as Millipore Fluoropore PTFE, Sterlitech NY125P, Pall Versapor (e.g., 450R or 800R), Millipore SureVent DVSP, Millipore SureVent DOHP, Millipore SureVent UPHP, or any other suitable polymeric membrane.

In certain instances, the membrane may be chosen to have an air flow rate of at least about 0.25 liter/(min cm$^2$ psi), and in some cases, at least about 0.275 liter/(min cm$^2$ psi), at least about 0.3 liter/(min cm$^2$ psi), at least about 0.4 liter/(min cm$^2$ psi), at least about 0.5 liter/(min cm$^2$ psi), at least about 0.6 liter/(min cm$^2$ psi), at least about 0.7 liter/(min cm$^2$ psi), at least about 0.8 liter/(min cm$^2$ psi), at least about 0.9 liter/(min cm$^2$ psi), at least about 1 liter/(min cm$^2$ psi), at least about 1.1 liter/(min cm² psi), at least about 1.2 liter/(min cm² psi), at least about 1.3 liter/(min cm² psi), or at least about 1.4 liter/(min cm² psi). (1 psi is about 7 kPa.) Higher air flow rates may be desirable in some embodiments. In addition, in some cases, a membrane having a relatively high bubble point is desired, e.g., a bubble point of at least about 5 psi, at least about 10 psi, or at least about 15 psi as measured for either water or blood.

Figure 10A:
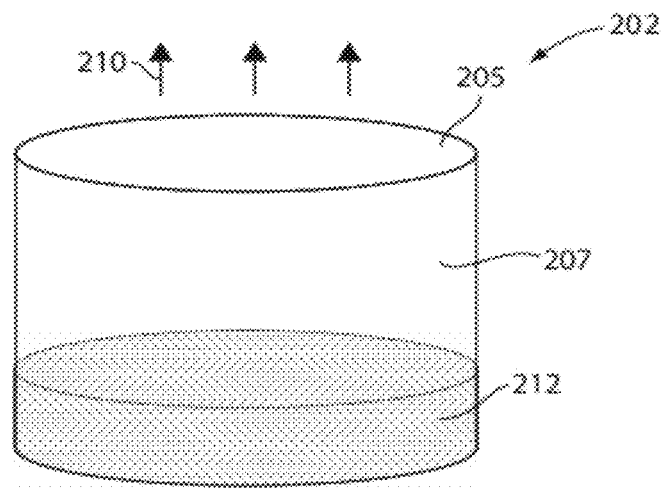
FIGS. 10A-10B illustrate certain membranes that can be used to at least partially confine liquids, in accordance with certain embodiments of the invention.
Figure 10B:
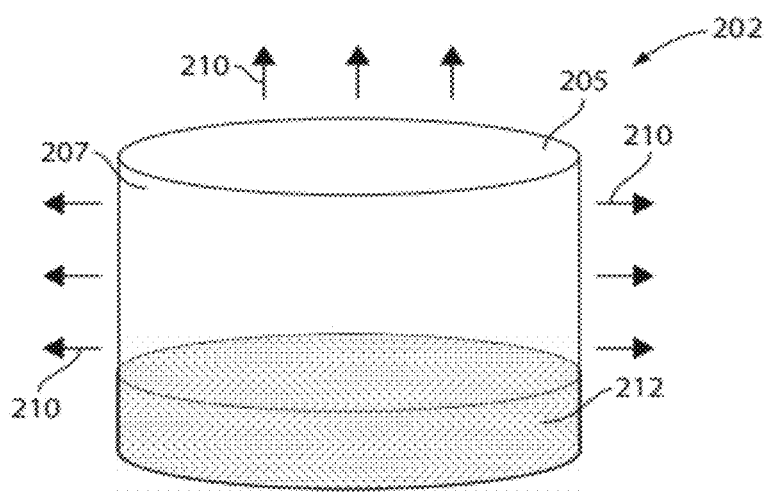

In some cases, the membrane may be used to form one or more surfaces defining the chamber for at least partially confining the liquid. For instance, referring to FIG. 10, in FIG. 10A, the top surface 205 of chamber 202 is formed from such membranes, and when liquid 212 enters chamber 202 (e.g., from below), air (or other gases) can leave through the top surface, as is indicated by arrows 210. However, in FIG. 10B, all of the surfaces 205, 207 of chamber 202 are formed from such membranes, thereby allowing air (or other gases) to leave from any or all of these surfaces, as indicated by arrows 210. This may be important, for example, in configurations where the device is tilted or held at an angle; even if liquid covers some portions of the chamber surface, there will be at least one surface formed from such membranes through which air or other gases are able to leave. Specific examples of devices with such configurations may be seen in U.S. and international patent applications, each entitled "Methods and Devices for Withdrawing Fluids from a Subject Using Reduced Pressure," each filed on even date herewith, each of which is incorporated herein by reference in its entirety. In addition, it should be noted that although FIG. 10 illustrates chambers having cylindrical configurations, this is by way of example only, and in other embodiments, other chamber configurations may be used, e.g., rectangular, cubical, spherical, etc.

Figure 2A:
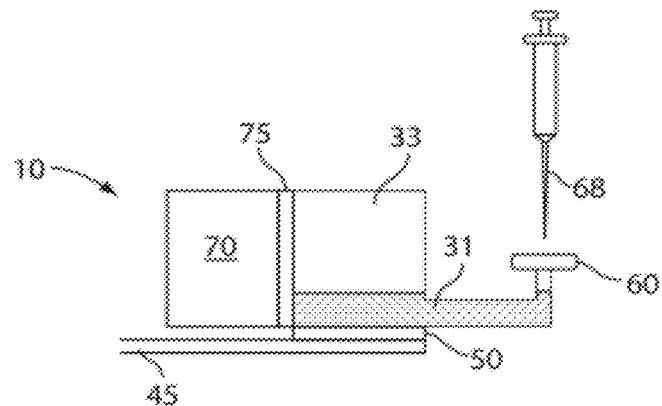
FIGS. 2A-2C illustrate the removal of a liquid from a device, in accordance with certain embodiments of the invention.
Figure 2B:
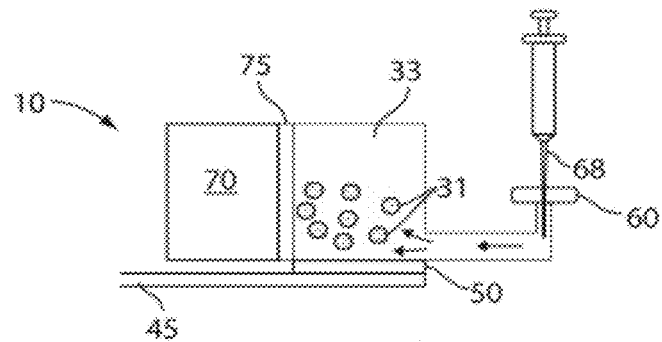

One non-limiting example of such a configuration is now described with reference to FIG. 2. In FIG. 2A, device 10 includes a storage chamber 33 containing a liquid therein 31 to be removed, for example, blood, plasma, serum, interstitial fluid, or the like. Optionally, membrane 50 may be present, which prevents liquid 31 from exiting storage chamber 33 through channel 45. Channel 45 may be, for example, a channel through which liquid 31 initially entered into storage chamber 33. In other embodiments, other suitable systems may be used to prevent liquid 31 from exiting storage chamber 33 through channel 45, for example, a valve such as a check valve or a flap valve, a gate, a pump, etc., may be used, such as described herein. Also shown in this figure is vacuum chamber 70, which may be in gaseous communication with storage chamber 33, e.g., via membrane 75. Due to the presence of membrane 75, gases are able to pass between vacuum chamber 70 and storage chamber 33, although liquids such as liquid 31 are not able to enter vacuum chamber 70.

Figure 2C:
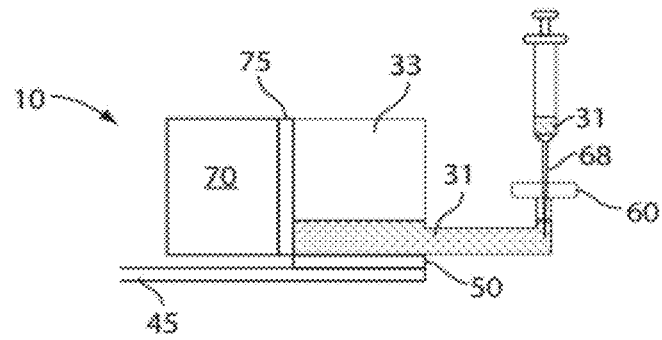

FIG. 2A also shows needle 68, which may be used to withdraw liquid 31 from storage chamber 33. Needle 68 is to be inserted into device 10 through septum 60 into storage chamber 33 and/or into a portion of device 10 that is in fluidic or liquid communication with the liquid within storage chamber 33, as is shown in this figure. However, needle 68 may contain a gas, typically air, which may be at atmospheric or ambient pressure. This pressure may be greater than the pressure within storage chamber 33. Accordingly, once needle 68 is inserted into septum 60, the gas within needle 68 is able to leave needle 68 and enter storage chamber 33. Depending on the difference in pressure, the gas in some embodiments may leave needle 68 relatively violently or in an uncontrolled fashion, thereby "blowing around" liquid 31 within storage chamber 33, as is shown representatively in FIG. 2B. However, due to the presence of membrane 75 and/or membrane 50, liquid 31 within storage chamber 33 is unable to leave the storage chamber, while gases are able to leave, e.g., entering vacuum chamber 70, until the pressures within needle 68, storage chamber 33, and vacuum chamber 70 have substantially equalized, so that liquid 31 no longer is moved or "blown around" due to any pressure imbalances within the device. Liquid 31 can then be drawn into needle 68 to be removed from device 10, as is shown in FIG. 2C.

In certain aspects, the device includes a fluid transporter able to withdraw fluid from the skin and/or beneath the skin of the subject into the device. As used herein, "fluid transporter" is any component or combination of components that facilitates movement of a fluid from one portion of the device to another, and/or from the device to the skin of the subject or vice versa. For example, at or near the skin, a fluid transporter can be or include a hollow needle or a solid needle, or other flow activator, and/or a region (applicator region) into which blood or other fluid is introduced. The flow activator may include a moveable mechanism, e.g., to move a needle, or may not require movement to function. For example, the flow activator may include a jet injector or a "hypospray" that delivers fluid under pressure to a subject, a pneumatic system that delivers and/or receives fluid, a hygroscopic agent that adsorbs or absorbs fluid, a reverse iontophoresis system, a transducer that emits ultrasonic waves, or thermal, radiofrequency and/or laser energy, and so on, any of which need not necessarily require movement of a flow activator to cause fluid release from a subject. If a solid needle is used, and fluid migrates along the needle due to surface forces (e.g., capillary action), then the solid needle can be at least a part of a fluid transporter. If fluid (e.g. blood or interstitial fluid) partially or fully fills an enclosure surrounding a needle after puncture of skin (whether the needle is or is not retracted from the skin after puncture), then the enclosure can define a fluid transporter. For example, the fluid transporter may include an applicator region such as is described herein (with or without a needle or other flow activator therein). Other components including partially or fully enclosed channels, microfluidic channels, tubes, wicking members, vacuum containers, etc. can be fluid transporters.

The fluid may be received from and/or through the skin of a subject (or other mucosal surface). The fluid transporter may be, for example, one or more needles and/or microneedles, a hygroscopic agent, a cutter or other piercing element, an electrically-assisted system, or the like, e.g., as discussed in detail herein. If needles or microneedles are used, they may be solid or hollow, i.e., blood, interstitial fluid, or other fluid may travel in and/or around the needles or microneedles into the device. In some cases, the needles or microneedles may also be removed from the skin of the subject, e.g., after insertion into the skin, for example, to increase the flow of blood or other fluids from the skin and/or beneath the skin of the subject. For example, one or more needles or microneedles may be inserted into the skin and removed, and then a pressure gradient or a vacuum may be applied to the skin to withdraw a fluid, such as blood or interstitial fluid. In one set of embodiments, the flow activator includes solid needles that are removed from the skin and a cup or channel may be used to direct the flow of blood or other bodily fluids.

Non-limiting examples of flow activators include one or more needles and/or microneedles, a hygroscopic agent, a cutter or other piercing element, an electrically-assisted system, or any other systems as described herein. Additional examples of such techniques are described herein and/or in the applications incorporated herein. It is to be understood that, generally, fluids may be received in a variety of ways, and various systems and methods for receiving fluid from the skin and/or beneath the skin are discussed below and/or in the applications incorporated herein. In one set of embodiments, techniques for piercing or altering the surface of the skin to transport a fluid are discussed, for example, using a needle such as a hypodermic needle or one or more microneedles, chemicals applied to the skin (e.g., penetration enhancers), jet injectors or other techniques such as those discussed below.

As an example, in one embodiment, a needle such as a hypodermic needle can be used to withdraw fluid to or from the skin and/or beneath the skin. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

If needles are present, there may be one or more needles, the needles may be of any suitable size and length, and the needles may each be solid or hollow. The needles may have any suitable cross-section (e.g., perpendicular to the direction of penetration), for example, circular, square, oval, elliptical, rectangular, rounded rectangle, triangular, polygonal, hexagonal, irregular, etc. For example, the needle may have a length of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. The needle may also have a largest cross-sectional dimension of less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 175 micrometers, less than about 150 micrometers, less than about 125 micrometers, less than about 100 micrometers, less than about 75 micrometers, less than about 50 micrometers, less than about 10 micrometers, etc. For example, in one embodiment, the needle may have a rectangular cross section having dimensions of 175 micrometers by 50 micrometers. In one set of embodiments, the needle may have an aspect ratio of length to largest cross-sectional dimension of at least about 2:1, at least about 3:1, at least about 4:1, at least about 5:1, at least about 7:1, at least about 10:1, at least about 15:1, at least about 20:1, at least about 25:1, at least about 30:1, etc.

In one embodiment, the needle is a microneedle. Typically, a microneedle will have an average cross-sectional dimension (e.g., diameter) of less than about a millimeter. It should be understood that references to "needle" or "microneedle" as discussed herein are by way of example and ease of presentation only, and that in other embodiments, more than one needle and/or microneedle may be present in any of the descriptions herein.

As an example, microneedles such as those disclosed in U.S. Pat. No. 6,334,856, issued Jan. 1, 2002, entitled "Microneedle Devices and Methods of Manufacture and Use Thereof," by Allen, et al., may be used to withdraw fluids (or other materials) from a subject. The microneedles may be hollow or solid, and may be formed from any suitable material, e.g., metals, ceramics, semiconductors, organics, polymers, and/or composites. Examples include, but are not limited to, medical grade stainless steel, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, polymethyl methacrylate, polyacrylic acid, or polyesters.

In some cases, more than one needle or microneedle may be used. For example, arrays of needles or microneedles may be used, and the needles or microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of needles or microneedles. In some embodiments, the device may have at least 3 but no more than 5 needles or microneedles (or other flow activators), at least 6 but no more than 10 needles or microneedles, or at least 11 but no more than 20 needles or microneedles. Typically, a microneedle will have an average cross-sectional dimension (e.g., diameter) of less than about a micron.

Those of ordinary skill in the art can arrange needles relative to the skin for these purposes including, in one embodiment, introducing needles into the skin at an angle, relative to the skin's surface, other than 90°, i.e., to introduce a needle or needles into the skin in a slanting fashion so as to limit the depth of penetration. In another embodiment, however, the needles may enter the skin at approximately 90°.

In some cases, the needles (or microneedles) may be present in an array selected such that the density of needles within the array is between about 0.5 needles/mm$^2$ and about 10 needles/mm$^2$, and in some cases, the density may be between about 0.6 needles/mm$^2$ and about 5 needles/mm$^2$, between about 0.8 needles/mm$^2$ and about 3 needles/mm$^2$, between about 1 needles/mm$^2$ and about 2.5 needles/mm$^2$, or the like. In some cases, the needles may be positioned within the array such that no two needles are closer than about 1 mm, about 0.9 mm, about 0.8 mm, about 0.7 mm, about 0.6 mm, about 0.5 mm, about 0.4 mm, about 0.3 mm, about 0.2 mm, about 0.1 mm, about 0.05 mm, about 0.03 mm, about 0.01 mm, etc.

In another set of embodiments, the needles (or microneedles) may be chosen such that the area of the needles (determined by determining the area of penetration or perforation on the surface of the skin of the subject by the needles) allows for adequate flow of fluid to or from the skin and/or beneath the skin of the subject. The needles may be chosen to have smaller or larger areas (or smaller or large diameters), so long as the area of contact for the needles to the skin is sufficient to allow adequate blood flow from the skin of the subject to the device. For example, in certain embodiments, the needles may be selected to have a combined skin-penetration area of at least about 500 nm$^2$, at least about 1,000 nm$^2$, at least about 3,000 nm$^2$, at least about 10,000 nm$^2$, at least about 30,000 nm$^2$, at least about 100,000 nm$^2$, at least about 300,000 nm$^2$, at least about 1 microns$^2$, at least about 3 microns$^2$, at least about 10 microns$^2$, at least about 30 microns$^2$, at least about 100 microns$^2$, at least about 300 microns$^2$, at least about 500 microns$^2$, at least about 1,000 microns$^2$, at least about 2,000 microns$^2$, at least about 2,500 microns$^2$, at least about 3,000 microns$^2$, at least about 5,000 microns$^2$, at least about 8,000 microns$^2$, at least about 10,000 microns$^2$, at least about 35,000 microns$^2$, at least about 100,000 microns$^2$, at least about 300,000 microns$^2$, at least about 500,000 microns$^2$, at least about 800,000 microns$^2$, at least about 8,000,000 microns$^2$, etc., depending on the application.

The needles or microneedles may have any suitable length, and the length may be, in some cases, dependent on the application. For example, needles designed to only penetrate the epidermis may be shorter than needles designed to also penetrate the dermis, or to extend beneath the dermis or the skin. In certain embodiments, the needles or microneedles may have a maximum penetration into the skin of no more than about 3 mm, no more than about 2 mm, no more than about 1.75 mm, no more than about 1.5 mm, no more than about 1.25 mm, no more than about 1 mm, no more than about 900 microns, no more than about 800 microns, no more than about 750 microns, no more than about 600 microns, no more than about 500 microns, no more than about 400 microns, no more than about 300 microns, no more than about 200 microns, no more than about 175 micrometers, no more than about 150 micrometers, no more than about 125 micrometers, no more than about 100 micrometers, no more than about 75 micrometers, no more than about 50 micrometers, etc. In certain embodiments, the needles or microneedles may be selected so as to have a maximum penetration into the skin of at least about 50 micrometers, at least about 100 micrometers, at least about 300 micrometers, at least about 500 micrometers, at least about 1 mm, at least about 2 mm, at least about 3 mm, etc.

In one set of embodiments, the needles (or microneedles) may be coated. For example, the needles may be coated with a substance that is delivered when the needles are inserted into the skin. For instance, the coating may comprise heparin, an anticoagulant, an anti-inflammatory compound, an analgesic, an anti-histamine compound, etc. to assist with the flow of blood from the skin of the subject, or the coating may comprise a drug or other therapeutic agent such as those described herein. The drug or other therapeutic agent may be one used for localized delivery (e.g., of or proximate the region to which the coated needles or microneedles are applied), and/or the drug or other therapeutic agent may be one intended for systemic delivery within the subject.

In one embodiment, the fluid is received manually, e.g., by manipulating a plunger on a syringe. In another embodiment, the fluid can be received from the skin and/or beneath the skin mechanically or automatically, e.g., using a piston pump or the like. Fluid may also be received using vacuums such as those discussed herein. For example, vacuum may be applied to a conduit, such as a needle, in fluidic communication with a bodily fluid in order to draw up at least a portion of the fluid from the skin. In yet another embodiment, fluid is received using capillary action (e.g., using a microfluidic channel or hypodermic needle having a suitably narrow inner diameter). In still another embodiment, pressure may be applied to force fluid out of the needle.

In some embodiments, fluid may be received using a hygroscopic agent applied to the surface of the skin or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be received from the skin and/or beneath the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the receiving of fluid from the skin and/or from beneath the skin. In one embodiment, a cutter is used to create such a pathway and removed, then fluid may be received via this pathway. In another embodiment, the cutter remains in place within the skin, and fluid may be received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a permselective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby withdrawing a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device (flow activator) may comprise an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

In certain embodiments, the flow activator may be fastened on a support structure. In some cases, the support structure can bring the flow activator to the skin, and in certain instances, insert the fluid transport into the skin. For example, the flow activator can be moved mechanically, electrically (e.g., with the aid of a servo, which may be computer-controlled), pneumatically, via a piston, a screw, a mechanical linkage, or the like. In one set of embodiments, the support structure can insert the flow activator into the skin at a speed of at least about 0.1 cm/s, at least about 0.3 cm/s, about 1 cm/s, at least about 3 cm/s, at least about 10 cm/s, at least about 30 cm/s, at least about 1 m/s, at least about 2 m/s, at least about 3 m/s, at least about 4 m/s, at least about 5 m/s, at least about 6 m/s, at least about 7 m/s, at least about 8 m/s, at least about 9 m/s, at least about 10 m/s, at least about 12 m/s, etc., at the point where the flow activator initially contacts the skin. Without wishing to be bound by any theory, it is believed that relatively faster insertion speeds may increase the ability of the flow activator to penetrate the skin (without deforming the skin or causing the skin to move in response), and/or decrease the amount of pain felt by the application of the flow activator to the skin. Any suitable method of controlling the penetration speed into the skin may be used, include those described herein.

Thus in some aspects, the device may include a support structure for application to the skin of the subject. The support structure may be used, as discussed herein, for applying the flow activator to the surface of the skin of the subject, e.g., so that fluid may be received from the skin and/or beneath the skin of the subject. In some cases, the support structure may immobilize the flow activator such that the flow activator cannot move relative to the support structure; in other cases, however, the flow activator may be able to move relative to the support structure. In one embodiment, as a non-limiting example, the flow activator is immobilized relative to the support structure, and the support structure is positioned within the device such that application of the device to the skin causes at least a portion of the flow activator to pierce the skin of the subject. In some cases, as discussed herein, the support structure includes a reversibly deformable structure.

In one set of embodiments, the support structure, or a portion of the support structure, may move from a first position to a second position. For example, the first position may be one where the support structure has immobilized relative thereto a flow activator that does not contact the skin (e.g., the flow activator may be contained within a recess), while the second position may be one where the flow activator does contact the skin, and in some cases, the flow activator may pierce the skin. The support structure may be moved using any suitable technique, e.g., manually, mechanically, electromagnetically, using a servo mechanism, or the like. In one set of embodiments, for example, the support structure may be moved from a first position to a second position by pushing a button on the device, which causes the support structure to move (either directly, or indirectly, e.g., through a mechanism linking the button with the support structure). Other mechanisms (e.g., dials, levers, sliders, etc., as discussed herein) may be used in conjunction with or instead of a button. In another set of embodiments, the support structure may be moved from a first position to a second position automatically, for example, upon activation by a computer, upon remote activation, after a period of time has elapsed, or the like. For example, in one embodiment, a servo connected to the support structure is activated electronically, moving the support structure from the first position to the second position.

In some cases, the support structure may also be moved from the second position to the first position. For example, after fluid has been received from the skin and/or beneath the skin, e.g., using a flow activator the support structure may be moved, which may move the flow activator away from contact with the skin. The support structure may be moved from the second position to the first position using any suitable technique, including those described above, and the technique for moving the support structure from the second position to the first position may be the same or different as that moving the support structure from the first position to the second position.

In one set of embodiments, the device may include a flexible concave member or a reversibly deformable structure that is moveable between a first configuration and a second configuration. For instance, the first configuration may have a concave shape, such as a dome shape, and the second configuration may have a different shape, for example, a deformed shape (e.g., a "squashed dome"), a convex shape, an inverted concave shape, or the like. The flexible concave member (or a reversibly deformable structure) may be moved between the first configuration and the second configuration manually, e.g., by pushing on the flexible concave member using a hand or a finger, and/or the flexible concave member may be moved using an actuator such as is described herein. In some cases, the flexible concave member may be able to spontaneously return from the second configuration back to the first configuration. In other cases, however, the flexible concave member may not be able to return to the first configuration, for instance, in order to prevent accidental repeated uses of the flexible concave member. The flexible concave member, in some embodiments, may be a reversibly deformable structure, although in other embodiments, it need not be.

The flexible concave member (or a reversibly deformable structure, in some embodiments) may be mechanically coupled to one or more needles (e.g., microneedles), or other flow activators such as those discussed herein. The needle may be directly immobilized on the flexible concave member, or the needles can be mechanically coupled to the flexible concave member using bars, rods, levers, plates, springs, or other suitable structures. The needle (or other flow activator), in some embodiments, is mechanically coupled to the flexible concave member such that the needle is in a first position when the flexible concave member is in a first configuration and the needle is in a second position when the flexible concave member is in a second configuration.

In some cases, relatively high speeds and/or accelerations may be achieved, and/or insertion of the needle may occur in a relatively short period of time, e.g., as is discussed herein. The first position and the second position, in some cases, may be separated by relatively small distances. For example, the first position and the second position may be separated by a distance of less than about 10 mm, less than about 9 mm, less than about 8 mm, less than about 7 mm, less than about 6 mm, less than about 5 mm, less than about 4 mm, less than about 3 mm, or less than about 2 mm, etc. However, even within such distances, in certain embodiments, high speeds and/or accelerations such as those discussed herein can be achieved.

During use, a device may be placed into contact with the skin of a subject such that a recess or other suitable applicator region is proximate or in contact with the skin. By moving the flexible concave member (or reversibly deformable structure) between a first configuration and a second configuration, because of the mechanical coupling, the flexible concave member is able to cause a needle (or other flow activator) to move to a second position within the recess or other applicator region and to contact or penetrate the skin of the subject.

In some embodiments, the device may also include a retraction mechanism able to move the needle (or other flow activator) away from the skin after the flexible concave member (or a reversibly deformable structure) reaches a second configuration. Retraction of the flexible concave member may, in some embodiments, be caused by the flexible concave member itself, e.g., spontaneously returning from the second configuration back to the first configuration, and/or the device may include a separate retraction mechanism, for example, a spring, an elastic member, a collapsible foam, or the like.

In some cases, the support structure may be able to draw skin towards the flow activator. For example, in one set of embodiments, the support structure may include a vacuum interface or region. The interface or region may be connected with a vacuum source (external and/or internal to the device), and when a vacuum is applied, skin may be drawn towards the support structure, e.g., for contact with a flow activator, such as one or more needles or microneedles.

In some cases, the device includes an interface that is able to apply vacuum to the skin. The interface may be, for example, a suction cup or a circular bowl that is placed on the surface of the skin, and vacuum applied to the interface to create a vacuum. In one set of embodiments, the interface is part of a support structure, as discussed herein. The interface may be formed from any suitable material, e.g., glass, rubber, polymers such as silicone, polyurethane, nitrile rubber, EPDM rubber, neoprene, or the like. In some cases, the seal between the interface and the skin may be enhanced (e.g., reducing leakage), for instance, using vacuum grease, petroleum jelly, a gel, or the like. In some cases, the interface may be relatively small, for example, having a diameter of less than about 5 cm, less than about 4 cm, less than about 3 cm, less than about 2 cm, less than about 1 cm, less than about 5 mm, less than about 4 mm, less than about 3 mm, less than about 2 mm, or less than about 1 mm. The interface may be circular, although other shapes are also possible, for example, square, star-shaped (having 5, 6, 7, 8, 9, 10, 11, etc. points), tear-drop, oval, rectangular, or the like.

In some cases, the support structure may be able to draw skin towards the flow activator. For example, in one set of embodiments, the support structure may include a vacuum interface. The interface may be connected with a vacuum source (external and/or internal to the device), and when a vacuum is applied, skin may be drawn towards the support structure, e.g., for contact with a flow activator, such as with one or more needles or microneedles. The interface may also be selected, in some cases, to keep the size of the contact region below a certain area, e.g., to minimize pain or discomfort to the subject, for aesthetic reasons, or the like. The interface may be constructed out of any suitable material, e.g., glass, plastic, or the like.

In one set of embodiments, the device includes a reversibly deformable structure able to drive a flow activator or a substance transfer component into the skin, e.g., so that the flow activator can withdraw a fluid from the skin and/or from beneath the skin of a subject. The reversibly deformable structure may be a structure that can be deformed using unaided force (e.g., by a human pushing the structure), or other forces (e.g., electrically-applied forces, mechanical interactions or the like), but is able to restore its original shape after the force is removed or at least partially reduced. For example, the structure may restore its original shape spontaneously, or some action (e.g., heating) may be needed to restore the structure to its original shape.

The reversibly deformable structure may be formed out a suitable elastic material, in some cases. For instance, the structure may be formed from a plastic, a polymer, a metal, etc. In one set of embodiments, the structure may have a concave or convex shape. For instance, the edges of the structure may be put under compressive stress such that the structure "bows" out to form a concave or convex shape. A person pushing against the concave or convex shape may deform the structure, but after the person stops pushing on the structure, the structure may be able to return to its original concave or convex shape, e.g., spontaneously or with the aid of other forces as previously discussed. In some cases, the device may be bistable, i.e., having two different positions in which the device is stable.

Figure 7:
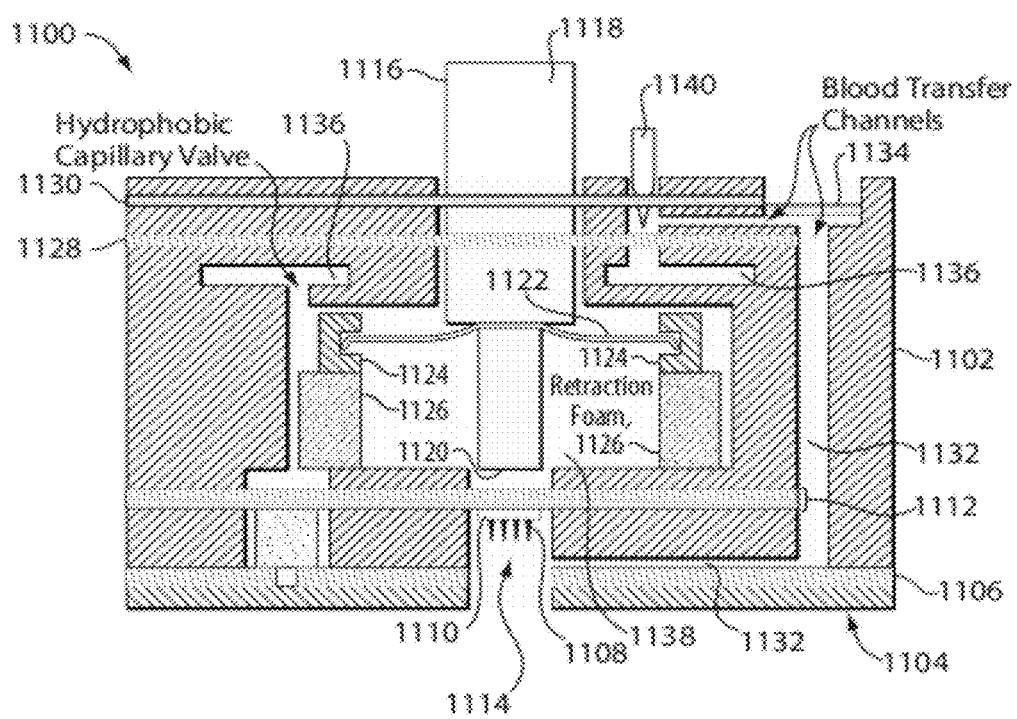
FIG. 7 illustrates yet another embodiment of the invention in which a device is actuated by a reversibly deformable structure.

An example of a reversibly deformable structure is now illustrated with respect to FIG. 7, which schematically illustrates device 1100 in which a flow activator comprising a substance transfer component is driven by a reversibly deformable structure. In FIG. 7, device 1100 includes a housing 1102 defining a plurality of chambers and channels. In other embodiments (not shown) a plurality of components that can be separable from and attachable to each other (e.g., modular components) can together define the device and together define a series of channels and compartments necessary for device function. See, e.g., U.S. patent application Ser. No. 12/716,233, filed Mar. 2, 2010, entitled "Systems and Methods for Creating and Using Suction Blisters or Other Pooled Regions of Fluid within the Skin," by Levinson, et al.; U.S. patent application Ser. No. 12/716,226, filed Mar. 2, 2010, entitled "Techniques and Devices Associated with Blood Sampling," by Levinson, et al.; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al.; or U.S. Provisional Patent Application Ser. No. 61/411,566, filed Nov. 9, 2010, entitled "Systems and Interfaces for Blood Sampling," by David Brancazio, each incorporated herein by reference.

In the specific device illustrated, device 1100 includes a surface 1104 for positioning the device proximate the skin of a subject during use. Where desired in certain embodiments, the device can include an adhesive layer 1106 where the adhesive is selected to be suitable for retaining the device in a relatively fixed position relative to the skin during use, but may allow for relatively easy removal of the device from the skin following use. Specific non-limiting examples of adhesives are discussed below. The adhesive also can be selected to assist in maintaining a vacuum within portions of the device proximate the skin as will be understood.

In FIG. 7, device 1100 includes a substance transfer component 1108. The substance transfer component may be, for example, a flow activator and/or a skin insertion object as discussed herein. Specific non-limiting examples include one or more needles or microneedles, e.g., as shown in FIG. 7. The substance transfer component can be, as described elsewhere herein and in other documents incorporated herein by reference, any of a variety of components able to withdraw a substance from the skin and/or from beneath the skin of a subject. For example, the substance transfer component may include one or more needles and/or microneedles, a hygroscopic agent, a cutter or other piercing element, an electrically-assisted system, or the like. In the specific device illustrated, substance transfer component 1108 defines an array of microinsertion objects such as solid or hollow microneedles. In one set of embodiments, substance transfer component 1108 is selected to have a particular size and profile for a particular use. For example, the substance transfer component may include an array of insertion or microinsertion objects which, in the device illustrated, emanate from a base 1110 which will be described further below.

In certain embodiments, a plurality of skin insertion objects define substance transfer component 1108 and are relatively small, and are relatively completely driven into the skin. Examples of skin insertion objects include needles or microneedles, e.g., as described in greater detail below. The skin insertion objects may be positioned to address the skin of the subject, each protruding from a base and defining a length from the base, and are able to be inserted into or through the skin to a depth essentially equal to their length but are prevented, by the base, from inserting at a depth greater than their length. In some embodiments, the plurality of skin insertion objects have an average length (measured from the base) of no more than about 1,000 microns or more than about 2,000 microns, although lengths can differ between individual skin insertion objects. In one set of embodiments, the skin insertion objects are of relatively uniform length, together defining an average length and each differing from the average length by no more than about 50%, about 40%, about 30%, about 10%, or about 5%, e.g., relative to the average length. The average length of the skin insertion objects, in other embodiments, are no more than about 1,500 microns, no more than about 1,000 microns, no more than about 900 microns, no more than about 800 microns, no more than about 750 microns, no more than about 600 microns, no more than about 500 microns, no more than about 400 microns, or no more than about 350 microns. In some embodiments, a triggering mechanism as discussed herein is provided that is able to move the skin insertion objects from a fully predeployed position to a fully deployed position with a force sufficient to insert the plurality of skin insertion object into or through the skin to an average depth of at least about 50% the average length of the plurality of skin insertion objects. In other embodiments, the triggering mechanism is able to insert the plurality of skin insertion objects to an average depth of at least about 55%, at least about 60%, at least about 65%, at least about 70%, at least about 75%, at least about 80%, at least about 85%, at least about 90%, at least about 92%, about 94%, about 96%, or about 98% of the average length of the plurality of skin insertion objects.

In the device illustrated, substance transfer component 1108 is mounted on a flexible structure 1112 which, as illustrated, is maintained relatively rigidly through various aspects of the device but which mounts substance transfer component 1108 flexibly for up/down movement relative to the skin. Flexible structure 1112 can be a membrane, a single or multi-layer structure selected from various polymers or the like to provide sufficient properties such as any combination of flexibility, elasticity, gas permeability or impermeability, fluid permeability or impermeability, or the like for desired operation. Portions of flexible structure 1112, substance transfer component 1108, and other interior walls of the device define a region 1114 which allows for movement of substance transfer component 1108 relative to the skin for receiving of a substance from the skin or beneath the skin, and, where a substance is received from the skin or from beneath the skin, region 1114 can serve as a reservoir for introduction of the substance into the device. Where a vacuum is used to withdraw a substance from the subject (e.g., as in the embodiment illustrated in FIG. 7), region 1114, when positioned against the skin, can expose vacuum to that portion of the skin proximate surface 1104 of the device and abutting the chamber.

Device 1100 also includes a transfer component actuator 1116 which, as illustrated, includes a proximate portion 1118 which can be addressed by a user of the device (who may be the same or different from the subject the device is administered to) and a distal portion 1120 for addressing substance transfer component 1108 via flexible structure 1112. Proximal portion 1118 and distal portion 1120 are, in the device illustrated, opposite ends of a single component but, as would be understood by those of ordinary skill in the art, the actuator can include a plurality of individual components operably linked in any way necessary to perform actuation as will be described.

As will be understood, FIG. 7 is a cross-section of a device illustrating various components and channels within the device. As will also be understood by those of ordinary skill in the art, different arrangements of devices and channels are contemplated herein so long as the purpose of the device described herein is met. In this figure, actuator 1116 is directly connected to or otherwise operably linked to a reversibly deformable structure 1122 which, in the device illustrated, is in the form of a "snap dome," the function and use of which will be described below. The snap dome in this figure has an approximately circular profile. The structure may define an interior and a periphery which, if not circular, may include a plurality of tabs, protrusions, or the like sufficient for support of structure 1122 within the device. As illustrated, a plurality of tabs (or the essentially circular perimeter of) the device are supported within holders 1124, and the center, snap dome portion of the device is operably linked to actuator 1116, such that movement of the central portion of snap dome 1122 and the periphery of the snap dome can be controlled independently of each other. Holders 1124 are directly connected to or otherwise operably linked to an actuator retraction component 1126 which, in the device illustrated, can be a ring-shaped structure positioned under and supporting holders 1124. Holders 1124 can be individual holders and/or a ring-like structure surrounding the periphery of snap dome 1122. A series of one, two, or more support members (e.g., 1130) are positioned near the top of device 1100 and serve to define a series of channels for sample flow, vacuum control, or the like as will be described.

Turning now to channels defined within the device, as described above, region 1114, when the device is positioned against skin, can serve to expose a portion of the skin defined by the periphery of the region to a vacuum, to substance transfer component 1108 as it moves toward and/or away from the skin, and/or to transfer a substance from or to the subject. Region 1114 can house a substance for transfer to the subject, in the form of a pharmaceutical composition or the like, optionally loaded on substance transfer component 1108. Where blood and/or interstitial fluid is drawn from a subject, region 1114 can serve to introduce the substance into the device from the subject.

A channel 1132 connects region 1114 to other portions of the device in this example. Channel 1132 can be used to deliver a substance to region 1114 for transfer to a subject, or for application of a vacuum to region 1114, and/or for receiving of a substance from a subject. The remainder of the description of device 1100 will be made within the context of receiving a substance such as blood and/or interstitial fluid from a subject, but it is to be understood that substances can also be delivered via various channels. Channel 1132 typically emanates in one direction from region 1114 although a plurality of channels can emanate from the region, arranged radially or otherwise relative to the center of the device. In device 1100, channel 1132 first passes laterally from the center of the device and then upwardly where, near the top of the device, it can, optionally, include one wall defining a window 1134 through which a user of the device can observe transfer of a substance, or through which analysis of a substance may occur. It can also itself define a reservoir, in whole or in part, or be connected to an internal or an external reservoir for maintaining, storing, and/or transferring a substance drawn from a subject. As shown here, it can be connected to a substance collection reservoir 1136 which, as illustrated, is a disc-shaped reservoir formed in the device housing and surrounding the center of the device including actuator 1116 and related components.

Device 1100, illustrated as one example of devices provided by the invention, includes a vacuum chamber for applying a vacuum proximate the skin of a subject for withdrawing a substance from the skin. As illustrated, vacuum chamber 1138 is positioned in a central portion of the device surrounding actuator 1116, although it can be provided anywhere in or proximate the device. The vacuum chamber can be evacuated to an appropriate level just prior to use, or the device can be pre-packaged under vacuum as described elsewhere herein. As illustrated, vacuum chamber 1138 is in fluid communication with substance collection reservoir 1136 but, in its initial state and prior to use, a membrane or other component, such as support member 1128, separates channel 1132 connecting it to region 1102. In the device illustrated, a vacuum actuation component 1140 can be actuated to puncture the membrane or other component (e.g., 1128) and thereby connect vacuum chamber 1138 with channel 1132, at an appropriate time during use of the device. In other embodiments, actuator 1116 and vacuum actuation component 1140 can be combined into a single button or operably linked so that only one operation is needed to actuate both the microinsertion objects and the vacuum.

Reversibly deformable structure (or, as shown, a snap dome) 1122 can be provided in a variety of forms including a monostable or bistable configuration. In the embodiment illustrated, a bistable configuration is illustrated including first and second low energy or stable configurations separated by a relatively high energy or unstable configuration. As shown, the reversibly deformable structure 1122 is shown in a "cocked" or predeployed position.

The reversibly deformable structure (or the flexible concave member) may be formed from any suitable material, for example, a metal such as stainless steel (e.g., 301, 301LN, 304, 304L, 304LN, 304H, 305, 312, 321, 321H, 316, 316L, 316LN, 316Ti, 317L, 409, 410, 430, 440A, 440B, 440C, 440F, 904L), carbon steel, spring steel, spring brass, phosphor bronze, beryllium copper, titanium, titanium alloy steels, chrome vanadium, nickel alloy steels (e.g., Monel 400, Monel K 500, Inconel 600, Inconel 718, Inconel x 750, etc.), a polymer (e.g., polyvinylchloride, polypropylene, polycarbonate, etc.), a composite or a laminate (e.g., comprising fiberglass, carbon fiber, bamboo, Kevlar, etc.), or the like.

The reversibly deformable structure may be of any shape and/or size. In one embodiment, the reversibly deformable structure is a flexible concave member. In some cases, the reversibly deformable structure may have a generally domed shape (e.g., as in a snap dome), and be circular (no legs), or the reversibly deformable structure may have other shapes, e.g., oblong, triangular (3 legs), square (4 legs), pentagonal (5 legs), hexagonal (6 legs), spider-legged, star-like, clover-shaped (with any number of lobes, e.g., 2, 3, 4, 5, etc.), or the like. The reversibly deformable structure may have, in some embodiments, a hole, dimple, or button in the middle. The reversibly deformable structure may also have a serrated disc or a wave shape. In some cases, a flow activator or a substance transfer component may be mounted on the reversibly deformable structure. In other cases, however, the flow activator or substance transfer component is mounted on a separate structure which is driven or actuated upon movement of the reversibly deformable structure.

In one set of embodiments, the reversibly deformable structure is not planar, and has a portion that can be in a first position (a "cocked" or predeployed position) or a second position (a "fired" or deployed position), optionally separated by a relatively high energy configuration. In some cases, both the first position and the second position are stable (i.e., the structure is bistable), although conversion between the first position and the second position requires the structure to proceed through an unstable configuration.

In some cases, surprisingly, the distance or separation between the first position and the second position is relatively small. Such distances or separations may be achieved using snap domes or other configurations such as those described herein, in contrast to springs or other devices which require longer translational or other movements. For example, the perpendicular distance (i.e., in a direction away from the skin) in the reversibly deformable structure between the top of the structure and the bottom of the structure (excluding the substance transfer component) when the device containing the structure is placed on the skin of a subject (i.e., the height of the device once it has been placed no the skin of the subject) may be no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm. In another set of embodiments, the reversibly deformable structure may have a greatest lateral dimension (parallel to the skin) when the device containing the structure is placed on the skin of a subject of no more than about 50 mm, no more than about 40 mm, no more than about 30 mm, no more than about 25 mm, no more than about 20 mm, no more than about 15 mm, no more than about 5 mm, no more than about 4 mm, no more than about 3 mm, no more than about 2 mm, no more than about 1 mm in some cases, no more than about 0.8 mm, no more than about 0.5 mm, or no more than about 0.3 mm. In one set of embodiments, the distance is between about 0.3 mm and about 1.5 mm.

In some embodiments, the device may exhibit a relatively high success rate of receiving of fluid from various subjects. For example, in some embodiments, the success rate of receiving at least about 5 microliters of blood from a subject may be at least about 95%, at least about 97%, at least about 98%, at least about 99%, or at least about 100%, as compared to prior art devices (e.g., lancet devices) which typically have success rates of less than 95%. In other embodiments, the volume may be at least about 0.1 microliters, at least about 0.3 microliters, at least about 0.5 microliters, at least about 1 microliter, at least about 3 microliters, at least about 5 microliters, or at least about 10 microliters. For instance, a population of subjects may be tested with both a prior art device and a device of the invention such that each subject is tested with both devices in a suitable location (e.g., the forearm) when determining success probabilities, where the population of subjects is randomly chosen. The population may be for example, at least 10, at least 100, at least 1,000, at least 10,000 or more individuals.

Use of device 1100 will now be described in the context of withdrawing a substance such as blood from a subject. Device 1100 is placed against the skin of a subject such that at least a portion of surface 1104 contacts the skin. Prior to use, a cover member (not shown) can cover surface 1104 of the device and can cover region 1114, to protect surface 1104 and region 1114 from contaminants, etc. optionally maintaining the interior of the device in a sterile condition. The cover can be peeled off or otherwise removed from the device, and the device placed against the skin, optionally adhering to the skin. Vacuum actuation component 1140 can be actuated to expose channel 1132 and region 1114 to vacuum at any time, including before, simultaneously, or after actuation of substance transfer component 1108. In one arrangement, vacuum actuation component 1140 is actuated to apply vacuum to region 1114 prior to actuation to substance transfer component 1108, thereby to create a vacuum against the skin proximate region 1114 prior to use. Actuation of actuator 1116 can take place before or after deployment of vacuum.

When transfer component actuator 1116 is actuated by a user (e.g., when proximal portion 1118 is depressed downwardly as shown in the figure), distal portion 1120 engages substance transfer component 1108 (optionally via flexible structure 1112) to drive it toward the skin. In some embodiments, foil 1128 is first broken, then component 1126 is compressed, before flexible structure 1112 is stretched and the reversibly deformable structure 1122 of the device fires or is actuated. Membranes or other members 1112, 1128, or 1130 may have, in some cases, sufficient flexibility and/or elasticity to allow actuator 1116 to drive substance transfer component 1108 sufficiently distally (downwardly, as shown) to engage the skin of the subject and carry out the desired function of the device. Various gaskets, bearings, or membranes as shown can be used for this function. Where support member 1128 is a foil or the like used for the purpose of initially separating vacuum reservoir 1138 from channel 1132 (e.g., prior to use), when actuator 1116 is moved downwardly, vacuum actuation component 1140 may rupture support member 1128 proximate actuator 1116, or flexibly deform as need be, so long as member 1130 (or another component) serves to allow actuator 1116 to slide within the device while maintaining sufficient vacuum in vacuum reservoir 1138 and related channels for use of the device.

When substance transfer component 1108 (e.g., insertion objects) engages the skin of the subject and facilitates receiving of a substance from the skin and/or from beneath the skin of the subject, a vacuum can draw the substance into region 1114, through channel or channels 1132, and into substance collection reservoir 1136. In this process, actuator 1116 first urges structure 1122 from its first stable configuration to a relatively unstable configuration and beyond that point, at which point the structure 1122 rapidly moves to a second stable configuration associated with downward driving of actuator 1116 to quickly drive access substance transfer component 1108 into and/or through the skin.

After that point, if it is desirable for access substance transfer component 1108 to be received from the skin, then a variety of techniques can be used to do so. In the device illustrated, retraction component 1126 drives holder 1124 upwardly, retracting structure 1122 and actuator 1116 from substance transfer component 1108. At that point, actuator 1116 can be operably linked to transfer component 1108 and withdraw the transfer component, or it can move freely relative to substance transfer component 1108, whereby flexible structure 1112 (e.g., an elastic membrane) or other component can withdraw substance transfer component 1108 from the skin. Again, in the device illustrated, retraction component 1126 can itself be a reversibly deformable structure such as a leaf spring, coil spring, foam, or the like. During use, when actuator 1116 is driven downwardly, retraction component 1126 is first compressed and, depending upon the size and arrangement of components 1126, 1124, 1122, 1116 and 1108, during compression, substance transfer component 1108 can be driven downwardly to some extent. At the point at which retraction component 1126 is compressed and provides a sufficient resistance force, reversibly deformable structure 1122 can be urged from its first configuration through an unstable configuration and can return to its second configuration, driving substance transfer component 1108 against the skin. Then, upon release of user pressure (or other actuation, which can be automatic) from actuator 1116, retraction component 1126 can expand and, with structure 1122 optionally remaining in its second, downwardly-driven low-energy configuration, actuator 1116 can be retracted and substance transfer component 1108 retracted from the skin.

Figure 8A:
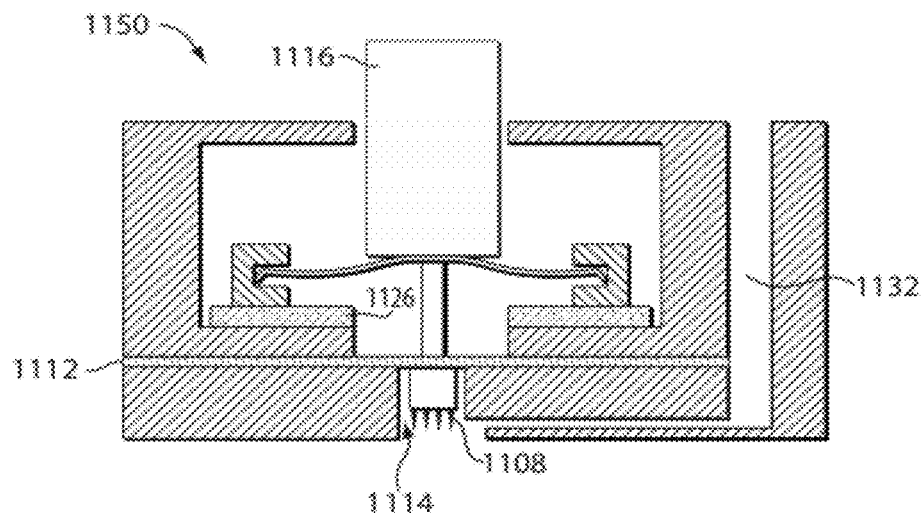
FIGS. 8A and 8B illustrate yet another embodiment of the invention, in which a device is actuated by a reversibly deformable structure, at different stages of operation of the device.
Figure 8B:
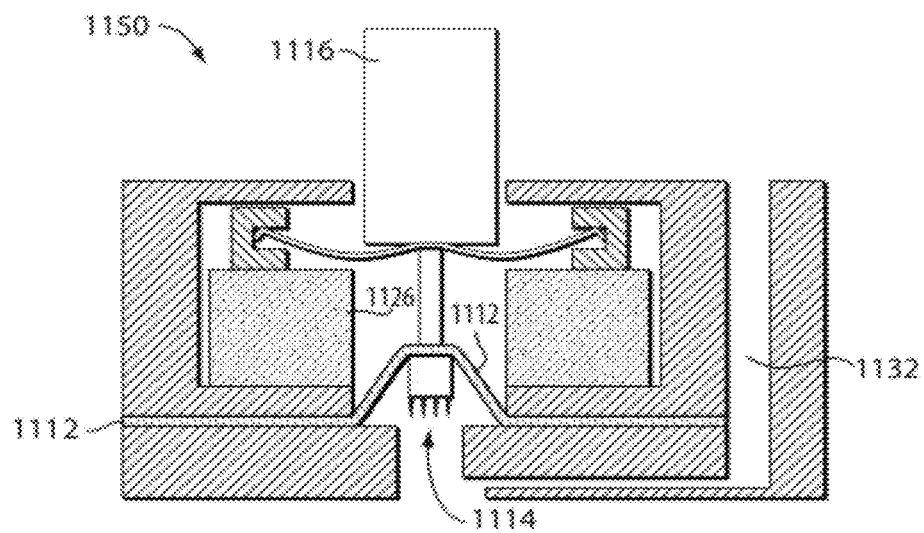

Referring now to FIGS. 8A and 8B, device 1150 is illustrated schematically. Device 1150 is similar to and can be considered essentially identical to device 1100 in all aspects other than those described here with respect to FIGS. 8A and 8B. As such, the reader will observe that not all components are provided, although other components similar to those of device 1100 can exist. One way in which device 1150 differs from device 1100 is that in device 1150, in the pre-deployment or post-deployment retracted configuration, membrane 1112 is drawn proximally (upwardly) as illustrated in FIG. 8B. Membrane 1112 is in a less-stressed lower-energy configuration as shown in FIG. 8A when retraction component 1126 is compressed and substance transfer component 1108 is driven into and/or through the skin. Devices 1100, 1150, and other similar devices are one way to enact a triggering mechanism that can move a substance transfer component 1108 or other similar transfer component relative to the skin in particularly advantageous ways. Examples of triggering mechanisms include, in addition to the examples shown in FIGS. 7 and 8, blasting caps, explosives, other chemical reactions, solenoids or other electrical interactions, pneumatics (e.g., compressed air), other thermal interactions or mechanical interactions, or the like.

In one set of embodiments, the triggering mechanism may move transfer component 1108 from a fully predeployed position (e.g., as shown in FIG. 7) to a fully deployed position in which substance transfer component 1108 is fully engaged with the skin, in a short period of time. In one embodiment, that period of time is less than about 0.01 seconds, and in other embodiments, less than about 0.009 seconds, less than about 0.008 seconds, less than about 0.007 seconds, less than about 0.006 seconds, less than about 0.005 seconds, less than about 0.004 seconds, less than about 0.003 seconds, less than about 0.002 seconds, less than about 0.001 seconds, less than about 0.0005 seconds, less than about 0.00025, or less than about 0.0001 seconds.

In another embodiment, substance transfer component 1108 moves quickly relative to skin during deployment via the triggering mechanism, reaching a speed of at least about 4 m/s, at least about 5 m/s, at least about 6 m/s, at least about 7 m/s, at least about 8 m/s, at least about 10 m/s, at least about 12 m/s, at least about 15 m/s, or at least about 20 m/s at the point at which substance transfer component 1108 first touches the skin during deployment.

In some cases, substance transfer component 1108 achieves relatively high accelerations due to the triggering mechanism, for example, at least about 4 m/s$^2$, about 6 m/s$^2$, about 8 m/s$^2$, about 10 m/s$^2$, about 12 m/s$^2$, about 15 m/s$^2$, or about 20 m/s$^2$, at least about 30 m/s$^2$, at least about 50 m/s$^2$, at least about 100 m/s$^2$, at least about 300 m/s$^2$, at least about 500 m/s$^2$, at least about 1,000 m/s$^2$, at least about 3,000 m/s$^2$, at least about 5,000 m/s$^2$, at least about 10,000 m/s$^2$, at least about 30,000 m/s$^2$, at least about 50,000 m/s$^2$, at least about 100,000 m/s$^2$, at least about 200,000 m/s$^2$, or at least about 300,000 m/s$^2$. In some embodiments, the substance transfer component 1108 is accelerated for relatively short periods of time, e.g., less than about 1 s, less than about 300 ms, less than about 100 ms, less than about 30 ms, less than about 10 ms, less than about 3 ms, or less than about 1 ms, and/or over relatively short distances, e.g., less than about 5 mm, less than about 4 mm, less than about 3 mm, less than about 2 mm, less than about 1 mm, less than about 800 micrometers, less than 600 micrometers, less than 500 micrometers, less than 400 micrometers, less than about 300 micrometers, less than about 200 micrometers, less than about 100 micrometers, less than about 50 micrometers, etc.

Significant forces can be applied to substance transfer component 1108 as it moves relative to the skin via the triggering mechanism. In one set of embodiments, substance transfer component 1108, at the point at which it first contacts the skin, is driven by a force created at least in part by the triggering mechanism of at least about 6 micronewtons, about 8 micronewtons, about 10 micronewtons, about 12 micronewtons, or about 15 micronewtons.

In another set of embodiments, substance transfer component 1108 applies a pressure to the skin, during deployment caused by the triggering mechanism, of at least about 100 N/m$^2$, at least about 300 N/m$^2$, at least about 1,000 N/m$^2$, at least about 3,000 N/m$^2$, etc. In force assessment, the area can be measured as the area of skin displaced by the transfer component at full deployment, e.g., the area of the skin ruptured by the total of the cross sectional area of all substance transfer components inserted into the skin, at the top surface of the skin.

In some cases, the substance transfer component is forced into the skin via the triggering mechanism with a force sufficient to insert the substance transfer component into or through the skin to an average depth of at least about 60% of the substance transfer component (or the average length of the substance transfer components, if more than one is used, e.g., as in an array of needles or microneedles). In some cases, the depth is at least about 65%, at least about 70%, at least about 75%, at least about 80%, at least about 85%, at least about 90%, or at least about 95% of the substance transfer component, e.g., the length of the needle or the microneedle inserted into the skin.

Devices of the invention can provide significant advantage in some embodiments. For example, triggering mechanisms able to move substance transfer components in short time periods, and/or at high velocities, and/or with high forces, and/or with high pressure, and/or drive relatively short substance transfer components such as microinsertion objects or microneedles relatively deeply into the skin and/or through the skin, and/or any combination of the above can provide significant advantage. In some embodiments, these features can provide better control of substance delivery or receiving. Better mechanical stability can be provided in some cases by shorter substance transfer components (e.g., bending and/or buckling can be avoided) and relatively shorter substance transfer components, designed to be driven relatively completely (for example, through nearly all of their entire length) into the skin may offer better control of penetration in some embodiments. If better control of penetration can be achieved, better delivery or receiving can also be achieved in some cases, for example, resulting in less pain or essentially painless deployment.

Moreover, if substance transfer components are used to deliver a substance such as a pharmaceutical composition into or through the skin, more precise delivery can be provided, according to certain embodiments. More precise control over depth of insertion of the substance transfer components (e.g., by using devices designed to insert the substance transfer components essentially fully) yield more control over the amount of pharmaceutical substance inserted into the skin by the substance transfer components, in some embodiments. Furthermore, quick and/or high velocity, and/or high force and/or pressure application of microinsertion objects to the skin may in certain embodiments result in lower pain or painless deployment.

Figure 9A:
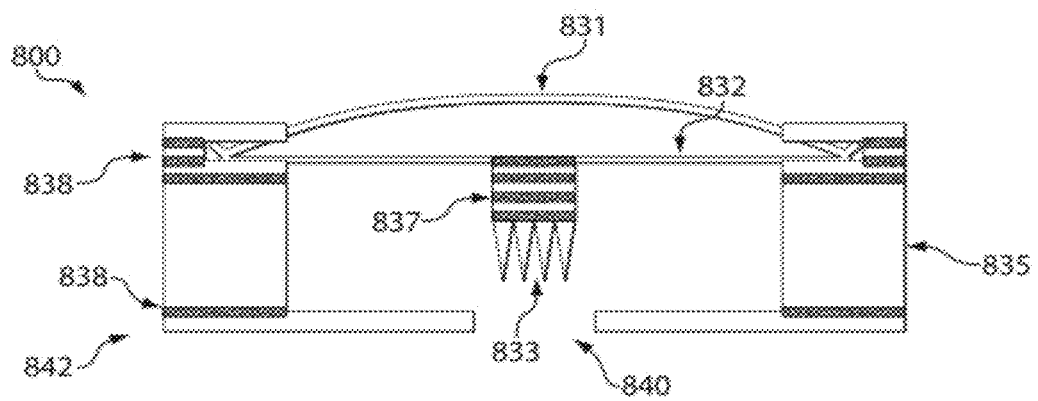
FIGS. 9A-9C illustrate various devices according to various embodiments of the invention.

Another example is illustrates in FIG. 9A. This figure shows a device 800 including a flow activator (e.g., microneedle array 833), a reversibly deformable structure (e.g., snap dome 832), an activator (e.g., activation button 831), a retraction mechanism (e.g., silicone foam 835), and structural components constructed from multiple layers of polycarbonate bonded together using a double-sided adhesive, such as 3M 1509 or 3M 1513 tape. The microneedle arrays can be bonded to laminated post 837 on the underside of a snap dome. Structural components 838, as well as post 837, are formed from polycarbonate and 3M 1509 or 3M 1513 adhesive. The arrays may range in needle number (4 to 28 needles), needle length (350 to 1000 micrometers), and/or arrangement (square, rectangular, and circular arrays), with array footprints of less than 3 mm in diameter, where the "footprint" is the area of the base to which the needles are attached.

In use, the device may be charged by setting the snap dome in a high energy position, placing the base of the device against the skin of a subject (with the needle tips pointing towards the skin), and pushing button 831 on the top of the device. As the button is pressed, silicone foam 835 compresses, positioning the needle tips in close proximity to the skin through opening 840. When the foam is fully compressed, the force causes the button to collapse, which then translates to the back of the snap dome to cause it to move to a stable low energy state. The release of energy from the snap dome changing states accelerates the microneedle array forward through the opening in the base and inserts the needles into the skin. When the force on the button is released, the silicone foam expands to its original height and retracts the needles from the skin in the process.

Figure 9B:
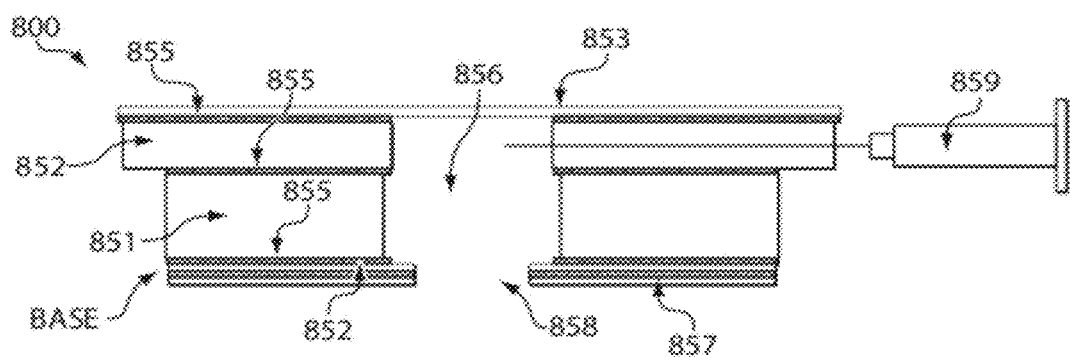

Yet another example is illustrates in FIG. 9B. This device includes a vacuum chamber comprising layers of polycarbonate, polyethylene terephthalate glycol (PETG), and silicone bonded together using a double-sided adhesive, such as 3M 1509 or 3M 1513 tape. The chamber is approximately 2.7 cm in diameter and 0.6 cm high, with cup opening 858 in the base that ranges from 3 to 7 mm in diameter. The vacuum chamber may be attached to the skin of a subject over the microneedle insertion site using adhesive 857, such as 3M 1509 or Katecho 10G hydrogel. A vacuum source (i.e., vacuum pump, syringe, vacuum reservoir, etc.) can be connected to the chamber using hypodermic needle 859 inserted through silicone layer 852, and vacuum (i.e., 30 to 70 kPa) may be applied to the site for a fixed period of time (i.e., 10 s to 10 min). The application of vacuum causes blood to flow from the skin punctures into the vacuum chamber.

Figure 9C:
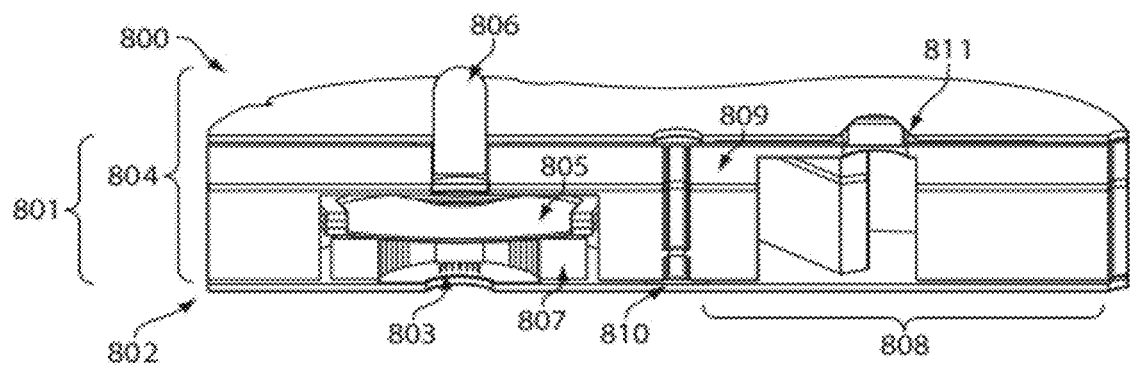

Still another example is shown in FIG. 9C. In this figure, the integrated device 800 includes a support structure 801 for application to the skin of the subject. The structure is constructed from multiple layers of polyethylene terephthalate glycol (PETG). These layers may be formed into the requisite geometry by machining sheet stock or injection molding. The individual layers are bonded together using double-sided adhesive, such as 3M 1513 tape, but may also be bonded using non-adhesive methods such as ultrasonic welding or laser welding. The support structure is attached to the skin of a subject using an adhesive 802, such as Katecho 10G hydrogel.

The left side of the support structure in FIG. 9C houses the components necessary to insert a microneedle array into the skin. These components include a circular microneedle array of sixteen 750 micrometers long needles 803 actuated by the extraction activator 804 comprising a reversibly deformable structure (e.g., a snap dome 805), a button 806, and a foam return mechanism 807. Pressing the button initially compresses the foam, bringing the microneedles into close proximity with the skin, and then fires the snap dome, moving it from the first stable configuration to the second stable configuration. The movement of the snap dome accelerates and inserts the microneedles into the skin. Releasing the pressure on the button allows the foam to expand and retract the microneedles from the skin.

The right side of the support structure shown in FIG. 9C comprises a self contained vacuum chamber 808 fluidically connected to a storage chamber 809. The storage chamber is fluidically connected to the extraction activator by a microfluidic channel 810. Pressing the button 811 breaks a seal and causes the fluidically connected components to be evacuated as well as reduces the pressure on the skin below the microneedle array. This reduced pressure urges blood from the skin into the microfluidic channel and into the storage chamber.

In certain aspects, the device may also contain an activator. The activator may be constructed and arranged to cause exposure of the flow activator to the skin upon activation of the activator. For example, the activator may cause a chemical to be released to contact the skin, one or more needles or microneedles to be driven into the skin, a vacuum to be applied to the skin, a jet of fluid to be directed to the skin, or the like. The activator may be activated by the subject, and/or by another person (e.g., a health care provider), or the device itself may be self-activating, e.g., upon application to the skin of a subject. The activator may be activated once, or multiple times in some cases. In some embodiments, the activator, or at least a portion thereof, may also serve as a seal, as discussed herein.

The device may be activated, for example, by pushing a button, flipping a switch, moving a slider, turning a dial, or the like. The subject, and/or another person, may activate the activator. In some cases, the device may be remotely activated. For example, a health care provider may send an electromagnetic signal which is received by the device in order to activate the device, e.g., a wireless signal, a Bluetooth signal, an Internet signal, a radio signal, etc.

Any or all of the arrangements described herein can be provided proximate a subject, for example on or proximate the skin of a subject, in various aspects. Activation of the devices can be carried out in a variety of ways, e.g., as described herein. For example, an on-skin device can be in the form of a patch or the like, optionally including multiple layers for activation, sensing, fluid flow, etc. In one embodiment, a patch or a device can be applied to a subject and a region of the patch or device activated (e.g., pushed, pressed, or tapped by a user) to inject a needle or a microneedle, or other flow activator, so as to access interstitial fluid or blood. The same or a different activation action, e.g., tapping or pushing action, can activate a vacuum source, open and/or close one or more of a variety of valves, or the like. The device can be a simple one in which it is applied to the skin and operates automatically (where e.g., application to the skin of the device allows access to interstitial fluid or blood, and delivers and/or withdraws fluid) or the patch or other device can be applied to the skin and one tapping or other activation action can cause fluid to flow through administration of one or more needles or microneedles (or other flow activator), opening of a valve, activation of vacuum, etc., or any combination thereof. Any number of activation actions can be carried out by a user repeatedly pushing, tapping, etc. a location or selectively, sequentially, and/or periodically activating a variety of switches.

In another arrangement, activation of one or more needles or microneedles, creation of suction blisters, opening and/or closing of valves, and other techniques to facilitate withdraw of a fluid can be carried out electronically or in other manners facilitated by the subject or by an outside controlling entity (e.g., another user of the device). For example, a device or patch can be provided proximate the skin of a subject and a radio frequency, electromagnetic, or other signal can be provided by a nearby controller or a distant source to activate any of the needles, flow activators, blister devices, valves, or other components of the devices described so that receiving of a fluid can be carried out as desired.

According to one aspect of the invention, the device is of a relatively small size. In some embodiments, the device may be sized such that it is wearable and/or carryable by a subject. For example, the device may be self-contained, needing no wires, cables, tubes, external structural elements, or other external support. The device may be positioned on any suitable position of the subject, for example, on the arm or leg, on the back, on the abdomen, etc.

In some embodiments, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

In another set of embodiments, the device may be an electrical and/or a mechanical device applicable or affixable to the surface of the skin, e.g., using adhesive, or other techniques such as those described herein. For example, in one set of embodiments, the device may include a support structure that contains an adhesive that can be used to immobilize the device to the skin. The adhesive may be permanent or temporary, and may be used to affix the device to the surface of the skin. The adhesive may be any suitable adhesive, for example, a pressure sensitive adhesive, a contact adhesive, a permanent adhesive, a cyanoacrylate, glue, gum, hot melts, an epoxy, a hydrogel, a hydrocolloid, or the like. In some cases, the adhesive is chosen to be biocompatible or hypoallergenic.

In another set of embodiments, the device may be mechanically held to the skin. For instance, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

Thus, in some embodiments, the device may be affixed or held onto the surface of the skin using any suitable technique, e.g., using adhesives, mechanical elements such as straps, belts, buckles, strings, ties, elastic bands, or the like. In some cases, the device may be positioned on the subject such that the subject is able to move around (e.g., walking, exercising, typing, writing, drinking or eating, using the bathroom, etc.) while wearing the device. For example, the device may have a mass and/or dimensions such that the subject is able to wear the device for at least about 5 minutes, and in some cases for longer periods of time, e.g., at least about 10 minutes, at least about 15 minutes, at least about 30 minutes, at least about 45 minutes, at least about 1 hour, at least about 3 hours, at least 5 hours, at least about 8 hours, at least about 1 day, at least about 2 days, at least about 4 days, at least about 1 week, at least about 2 weeks, at least about 4 weeks, etc.

In some embodiments, the device is relatively lightweight. For example, the device may have a mass of no more than about 1 kg, no more than about 300 g, no more than about 150 g, no more than about 100 g, no more than about 50 g, no more than about 30 g, no more than about 25 g, no more than about 20 g, no more than about 10 g, no more than about 5 g, or no more than about 2 g. For instance, in various embodiments, the device has a mass of between about 2 g and about 25 g, a mass of between about 2 g and about 10 g, a mass of between 10 g and about 50 g, a mass of between about 30 g and about 150 g, etc.

The device, in some cases, may be relatively small. For example, the device may be constructed and arranged to lie relatively close to the skin. Thus, for instance, the device may have a largest vertical dimension, extending from the skin of the subject when the device is positioned on the skin, of no more than about 25 cm, no more than about 10 cm, no more than about 7 cm, no more than about 5 cm, no more than about 4 cm, no more than about 3 cm, no more than about 2 cm, no more than about 1 cm, no more than about 8 mm, no more than about 5 mm, no more than about 3 mm, no more than about 2 mm, no more than about 1 mm, or no more than about 0.5 mm. In some cases, the device may have a largest vertical dimension of between about 0.5 cm and about 1 cm, between about 2 and about 3 cm, between about 2.5 cm and about 5 cm, between about 2 cm and about 7 cm, between about 0.5 mm and about 7 cm, etc.

In another set of embodiments, the device may have a relatively small size. For example, the device may have a largest lateral dimension (e.g., parallel to the skin) of no more than about 25 cm, no more than about 10 cm, no more than about 7 cm, no more than about 5 cm, no more than about 3 cm, no more than about 2 cm, or no more than about 1 cm. In some cases, the device may have a largest lateral dimension of between about 0.5 cm and about 1 cm, between about 2 and about 3 cm, between about 2.5 cm and about 5 cm, between about 2 cm and about 7 cm, etc.

Combinations of these and/or other dimensions are also possible in other embodiments. As non-limiting examples, the device may have a largest lateral dimension of no more than about 5 cm, a largest vertical dimension of no more than about 1 cm, and a mass of no more than about 25 g; or the device may have a largest lateral dimension of no more than about 5 cm, a largest vertical dimension of no more than about 1 cm, and a mass of no more than about 25 g; etc.

The device, in certain aspects, may contain a portion able to determine a fluid removed from the skin. For example, in some cases, a device can be applied to the skin, and activated to withdraw fluid from the skin and/or beneath the skin of the subject. The device, or a portion thereof, may then be processed to determine the fluid and/or an analyte within the fluid, alone or with an external apparatus. For example, fluid may be received from the device, and/or the device may contain sensors or agents able to determine the fluid and/or an analyte suspected of being contained in the fluid. For example, a portion of the device may contain a sensor, or reagents able to interact with an analyte contained or suspected to be present within the received fluid from the skin of the subject, for example, a marker for a disease state. For example, the sensor may determine plasma, serum, or blood that has been received from the subject.

The sensor may be embedded within or integrally connected to the device, or positioned remotely but with physical, electrical, and/or optical connection with the device so as to be able to sense a chamber within or fluid from the device. For example, the sensor may be in fluidic communication with fluid received from a subject, directly, via a microfluidic channel, an analytical chamber, etc. The sensor may be able to sense an analyte, e.g., one that is suspected of being in a fluid received from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a chamber within the device. As another example, a sensor may be positioned on or within the device, and may sense activity in a chamber by being connected optically to the chamber. Sensing communication can also be provided where the chamber is in communication with a sensor fluidly, optically or visually, thermally, pneumatically, electronically, or the like, so as to be able to sense a condition of the chamber. As one example, the sensor may be positioned downstream of a chamber, within a channel such a microfluidic channel, on an external apparatus, or the like.

Thus, the invention provides, in certain embodiments, sensors able to determine an analyte. Such determination may occur within the skin, and/or externally of the subject, e.g., within a device on the surface of the skin, depending on the embodiment. "Determine," in this context, generally refers to the analysis of a species, for example, quantitatively or qualitatively, and/or the detection of the presence or absence of the species. "Determining" may also refer to the analysis of an interaction between two or more species, for example, quantitatively or qualitatively, and/or by detecting the presence or absence of the interaction, e.g. determination of the binding between two species. The species may be, for example, a bodily fluid and/or an analyte suspected of being present in the bodily fluid. "Determining" also means detecting or quantifying interaction between species or identifying or otherwise assessing one or more characteristics of the sample, such as the presence and/or concentration of one or more species, a physical and/or chemical property of the sample, etc.

Fluids received from the skin and/or from beneath the skin of the subject will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. Still other analytes include, but not limited to, high-density lipoprotein ("HDL"), low-density lipoprotein ("LDL"), albumin, alanine transaminase ("ALT"), aspartate transaminase ("AST"), alkaline phosphatase ("ALP"), bilirubin, lactate dehydrogenase, etc. (e.g., for liver function tests); luteinizing hormone or beta-human chorionic gonadotrophin (hCG) (e.g., for fertility tests); prothrombin (e.g., for coagulation tests); troponin, BNT or B-type natriuretic peptide, etc., (e.g., as cardiac markers); infectious disease markers for the flu, respiratory syncytial virus or RSV, etc.; or the like.

The sensor may be, for example, a pH sensor, an optical sensor, an oxygen sensor, a sensor able to detect the concentration of a substance, or the like. Non-limiting examples of sensors useful in the invention include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other suitable sensors. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

Examples of sensors include, but are not limited to, pH sensors, optical sensors, ion sensors, colorimetric sensors, a sensor able to detect the concentration of a substance, or the like, e.g., as discussed herein. For instance, in one set of embodiments, the device may include an ion selective electrode. The ion selective electrode may be able to determine a specific ion and/or ions such as $K^+$, $H^+$, $Na^+$, $Ag^+$, $Pb^{2+}$, $Cd^{2+}$, or the like. Various ion selective electrodes can be obtained commercially. As a non-limiting example, a potassium-selective electrode may include an ion exchange resin membrane, using valinomycin, a potassium channel, as the ion carrier in the membrane to provide potassium specificity.

Examples of analytes that the sensor may be used to determine include, but are not limited to, pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, e.g., legal prescription levels of drugs such as coumadin, other drugs such as nicotine, or illegal drugs such as cocaine. Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever. Still other potentially suitable analytes include various pathogens such as bacteria or viruses, and/or markers produced by such pathogens.

As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the received fluid may be determined in some cases. Those of ordinary skill in the art will be aware of many suitable commercially-available sensors, and the specific sensor used may depend on the particular analyte being sensed. For instance, various non-limiting examples of sensor techniques include pressure or temperature measurements, spectroscopy such as infrared, absorption, fluorescence, UV/visible, FTIR ("Fourier Transform Infrared Spectroscopy"), or Raman; piezoelectric measurements; immunoassays; electrical measurements, electrochemical measurements (e.g., ion-specific electrodes); magnetic measurements, optical measurements such as optical density measurements; circular dichroism; light scattering measurements such as quasielectric light scattering; polarimetry; refractometry; chemical indicators such as dyes; or turbidity measurements, including nephelometry.

In one set of embodiments, a sensor in the device may be used to determine a condition of the blood, interstitial fluid, or other fluid present within the device. For example, the sensor may indicate the condition of analytes commonly found within the blood or interstitial fluid, for example, $O_2$, $K^+$, hemoglobin, $Na^+$, glucose, or the like. As a specific non-limiting example, in some embodiments, the sensor may determine the degree of hemolysis within blood contained within the device. Without wishing to be bound by any theory, it is believed that in some cases, hemolysis of red blood cells may cause the release of potassium ions and/or free hemoglobin into the blood. By determining the levels of potassium ions, and/or hemoglobin (e.g., by subjecting the device and/or the blood to separate cells from plasma, then determining hemoglobin in the plasma using a suitable colorimetric assay), the amount of blood lysis or "stress" experienced by the blood contained within the device may be determined. Accordingly, in one set of embodiments, the device may indicate the usability of blood (or other fluid) contained within the device, e.g., by indicating the degree of stress or the amount of blood lysis. Other examples of devices suitable for indicating the usability of blood (or other fluid) contained within the device are also discussed herein (e.g., by indicating the amount of time blood has been contained in the device, the temperature history of the device, etc.).

In some embodiments, an analyte may be determined as an "on/off" or "normal/abnormal" situation. Detection of the analyte, for example, may be indicative that insulin is needed; a trip to the doctor to check cholesterol; ovulation is occurring; kidney dialysis is needed; drug levels are present (e.g., especially in the case of illegal drugs) or too high/too low (e.g., important in care of geriatrics in particular in nursing homes). As another embodiment, however, an analyte may be determined quantitatively.

In some cases, fluids received from the subject, such as plasma or serum, will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. As discussed herein, certain embodiments of the present invention are generally directed at methods for receiving fluids from the body, and optionally determining one or more analytes within the received fluid. Thus, in some embodiments, at least a portion of the fluid may be stored, and/or analyzed to determine one or more analytes, e.g., a marker for a disease state, or the like. The fluid received from the skin and/or beneath the skin may be subjected to such uses, and/or one or more materials previously delivered to the skin may be subject to such uses.

Still other potentially suitable analytes include various pathogens such as bacteria or viruses, and/or markers produced by such pathogens. Thus, in certain embodiments of the invention, as discussed below, one or more analytes may be determined in some fashion, which may be useful in determining a past, present and/or future condition of the subject.

In one set of embodiments, the sensor may be a test strip, for example, test strips that can be obtained commercially. Examples of test strips include, but are not limited to, glucose test strips, urine test strips, pregnancy test strips, or the like. A test strip will typically include a band, piece, or strip of paper or other material and contain one or more regions able to determine an analyte, e.g., via binding of the analyte to a diagnostic agent or a reaction entity able to interact with and/or associate with the analyte. For example, the test strip may include various enzymes or antibodies, glucose oxidase and/or ferricyanide, or the like. The test strip may be able to determine, for example, glucose, cholesterol, creatinine, ketones, blood, protein, nitrite, pH, urobilinogen, bilirubin, leucocytes, luteinizing hormone, etc., depending on the type of test strip. The test strip may be used in any number of different ways. In some cases, a test strip may be obtained commercially and inserted into the device, e.g., before or after withdrawing blood, interstitial fluid, or other fluids from a subject. At least a portion of the blood or other fluid may be exposed to the test strip to determine an analyte, e.g., in embodiments where the device uses the test strip as a sensor so that the device itself determines the analyte. In some cases, the device may be sold with a test strip pre-loaded, or a user may need to insert a test strip in a device (and optionally, withdraw and replace the test strip between uses). In certain cases, the test strip may form an integral part of the device that is not removable by a user. In some embodiments, after exposure to the blood or other fluid received from the subject, the test strip may be removed from the device and determined externally, e.g., using other apparatuses able to determine the test strip, for example, commercially-available test strip readers.

As mentioned, in some aspects, the device may include channels such as microfluidic channels. In some cases, the microfluidic channels are in fluid communication with a flow activator that is used to deliver to and/or withdraw fluids from the skin and/or beneath the skin. For example, in one set of embodiments, the device may include a hypodermic needle or other needle (e.g., one or more microneedles) that can be inserted into the skin, and fluid may be delivered into or through the skin via the needle and/or received from the skin via the needle. The device may also include one or more microfluidic channels to contain fluid for delivery to the needle, e.g., from a source of fluid, and/or to withdraw fluid received from the skin and/or beneath the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For examples, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio (length to average cross-sectional dimension), e.g., an aspect ratio of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

As mentioned, in accordance with some aspects, blood, plasma, serum, interstitial fluid, or other bodily fluids may be stored within the device for later use and/or analysis. For instance, the device may include a storage chamber having an internal pressure less than atmospheric or ambient pressure prior to receiving blood, plasma, serum, interstitial fluid, or other bodily fluids. In certain embodiments, relatively small storage chambers may be used, e.g., so that the device may have a relatively small size. For example, the storage chamber may have a volume of less than about 25 ml, less than about 20 ml, less than about 15 ml, less than about 10 ml, less than about 5 ml, less than about 3 ml, less than about 2 ml, or less than about 1 ml.

In one set of embodiments, the device may include an anticoagulant or a stabilizing agent for stabilizing the fluid received from the skin and/or beneath the skin, e.g., within the storage chamber. For example, the fluid may be stored within the device for a certain period of time, and/or the device (or a portion thereof) may be moved or shipped to another location for analysis or later use. For instance, a device may contain anticoagulant or a stabilizing agent in a storage chamber. In some cases, more than one anticoagulant may be used, e.g., in the same storage chamber, or in more than one storage chamber.

The device may include an anticoagulant or a stabilizing agent for stabilizing the fluid received from the skin and/or beneath the skin. As a specific non-limiting example, an anticoagulant may be used for blood received from the skin. Examples of anticoagulants include, but are not limited to, heparin, citrate, thrombin, oxalate, ethylenediaminetetraacetic acid (EDTA), sodium polyanethol sulfonate, acid citrate dextrose. Other agents may be used in conjunction with or instead of anticoagulants, for example, stabilizing agents such as solvents, diluents, buffers, chelating agents, antioxidants, binding agents, preservatives, antimicrobials, or the like. Examples of preservatives include, for example, benzalkonium chloride, chlorobutanol, parabens, or thimerosal. Non-limiting examples of antioxidants include ascorbic acid, glutathione, lipoic acid, uric acid, carotenes, alpha-tocopherol, ubiquinol, or enzymes such as catalase, superoxide dismutase, or peroxidases. Examples of microbials include, but are not limited to, ethanol or isopropyl alcohol, azides, or the like. Examples of chelating agents include, but are not limited to, ethylene glycol tetraacetic acid or ethylenediaminetetraacetic acid. Examples of buffers include phosphate buffers such as those known to ordinary skill in the art.

In one set of embodiments, at least a portion of the device may be colored to indicate the anticoagulant(s) contained within the device. In some cases, the colors used may be identical or equivalent to that commercially used for Vacutainers™, Vacuettes™, or other commercially-available phlebotomy equipment. For example, lavender and/or purple may indicate ethylenediaminetetraacetic acid, light blue may indicate citrate, dark blue may indicate ethylenediaminetetraacetic acid, green may indicate heparin, gray may indicate a fluoride and/or an oxalate, orange may indicate a thrombin, yellow may indicate sodium polyanethol sulfonate and/or acid citrate dextrose, black may indicate citrate, brown may indicate heparin, etc. In other embodiments, however, other coloring systems may be used.

Other coloring systems may be used in other embodiments of the invention, not necessarily indicative of anti-coagulants. For example, in one set of embodiments, the device carries a color indicative of a recommended bodily use site for the device, e.g., a first color indicative of a device suitable for placement on the back, a second color indicative of a device suitable for placement on a leg, a third color indicative of a device suitable for placement on the arm, etc.

As mentioned, in one set of embodiments, a device of the invention as discussed herein may be shipped to another location for analysis. In some cases, the device may include an anticoagulant or a stabilizing agent contained within the device, e.g., within a storage chamber for the fluid. Thus, for example, fluid such as blood or interstitial fluid received from the skin and/or beneath the skin may be delivered to a chamber (e.g., a storage chamber) within the device, then the device, or a portion of the device (e.g., a module) may be shipped to another location for analysis. Any form of shipping may be used, e.g., via mail.

In some embodiments, the device may be attached to a suitable external apparatus able to analyze a portion of the device (e.g., containing a fluid, such as blood, serum, or plasma), and/or the external apparatus may remove at least some of the blood, plasma, serum, or other fluid from the device for subsequent analysis and/or storage. In some cases, however, at least some analysis may be performed by the device itself, e.g., using one or more sensors, etc., contained within the device. In some cases, the chambers may be in fluidic communication with one or more flow activators and/or one or more microfluidic channels. For instance, the device may contain a chamber for collecting fluid received from a subject (e.g., for storage and/or later analysis), a chamber for containing a fluid for delivery to the subject (e.g., blood, saline, optionally containing drugs, hormones, vitamins, pharmaceutical agents, or the like), etc.

For example, as discussed in detail below, in some cases, a storage chamber may contain a reagent or a reaction entity able to react with an analyte suspected of being present in the blood (or other fluid, e.g., plasma or serum) entering the device, and in some cases, the reaction entity may be determined to determine the analyte. In some cases, the determination may be made externally of the device, e.g., by determining a color change or a change in fluorescence, etc. The determination may be made by a person, or by an external apparatus able to analyze at least a portion of the device. In some cases, the determination may be made without removing blood, serum, or plasma from the device, e.g., from the storage chamber. (In other cases, however, blood or other fluids may first be removed from the device before being analyzed.) For example, the device may include one or more sensors (e.g., ion sensors such as $K^+$ sensors, colorimetric sensors, fluorescence sensors, etc.), and/or contain "windows" that allow light to penetrate the device. The windows may be formed of glass, plastic, etc., and may be selected to be at least partially transparent to one or a range of suitable wavelengths, depending on the analyte or condition to be determined. As a specific example, the entire device (or a portion thereof) may be mounted in an external apparatus, and light from the external apparatus may pass through or otherwise interact with at least a portion of the device (e.g., be reflected or refracted via the device) to determine the analyte and/or the reaction entity.

After withdraw of the fluid into the device, the device, or a portion thereof, may be removed from the skin of the subject, e.g., by the subject or by another person. For example, the entire device may be removed, or a portion of the device containing the storage reservoir may be removed from the device, and optionally replaced with another storage reservoir. Thus, for instance, in one embodiment, the device may contain two or more modules, for example, a first module that is able to cause receiving of fluid from the skin into a storage reservoir, and a second module containing the storage module. In some cases, the module containing the storage reservoir may be removed from the device. Other examples of modules and modular systems are discussed herein; still other examples are discussed in U.S. Provisional Patent Application Ser. No. 61/256,931, filed Oct. 30, 2009, entitled "Modular Systems for Application to the Skin," incorporated by reference herein in its entirety.

The received fluid may then be sent to a clinical and/or laboratory setting, e.g., for analysis. In some embodiments, the entire device may be sent to the clinical and/or laboratory setting; in other embodiments, however, only a portion of the device (e.g., a module containing a storage reservoir containing the fluid) may be sent to the clinical and/or laboratory setting. In some cases, the fluid may be shipped using any suitable technique (e.g., by mail, by hand, etc.). In certain instances, the subject may give the fluid to appropriate personnel at a clinical visit. For instance, a doctor may prescribe a device as discussed above for use by the subject, and at the next doctor visit, the subject may give the doctor the received fluid, e.g., contained within a device or module.

In one aspect, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered to and/or received from the skin and/or beneath the skin, based on a condition of the device, or the like. The signal may represent any suitable data or image. For example, the signal may represent the presence and/or concentration of an analyte in fluid received from a subject, the amount of fluid received from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in one set of embodiments, an image of the signal (e.g., a visual image or photograph) can be obtained and transmitted to a different entity (for example, a user can take a cell phone picture of a signal generated by the device and send it, via cell phone, the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. A signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the skin of the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch or other device can be worn by a subject to determine presence and/or amount of one or more analytes qualitatively, quantitatively, and/or over time. The subject can visit a clinician who can remove the patch or a portion of the patch (or other device) and attach it to a medical record associated with the subject.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a polyester, a fluorinated derivative of a polyimide, or the like. Another example is polyethylene terephthalate glycol ("PETG"). In PETG, the ethylene glycol group that is normally part of the PET chain is partially substituted for cyclohexane dimethanol (e.g., approximately 15-35 mol % of the ethylene groups are replaced), which may, in some cases, slow down the crystallization of the polymer when injection molded to allow better processing. Combinations, copolymers, derivatives, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In another aspect, the present invention is directed to a kit including one or more of the compositions previously discussed, e.g., a kit including a device for the delivery to and/or receiving of fluid from the skin and/or beneath the skin, a kit including a device able to create a pooled region of fluid within the skin of a subject, a kit including a device able to determine a fluid, or the like. A "kit," as used herein, typically defines a package or an assembly including one or more of the compositions or devices of the invention, and/or other compositions or devices associated with the invention, for example, as previously described. For example, in one set of embodiments, the kit may include a device and one or more compositions for use with the device. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In one set of embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. patent application Ser. No. 12/478,756, filed Jun. 4, 2009, entitled "Compositions and Methods for Diagnostics, Therapies, and Other Applications," by Levinson, published as U.S. Pat. Apl. Pub. No. 2010/0069726 on Mar. 18, 2010; U.S. patent application Ser. No. 12/716,222, filed Mar. 2, 2010, entitled "Oxygen Sensor," by Levinson, et al., published as U.S. Pat. Apl. Pub. No. 2010/0249560 Sep. 30, 2010; U.S. patent application Ser. No. 12/716,233, filed Mar. 2, 2010, entitled "Systems and Methods for Creating and Using Suction Blisters or Other Pooled Regions of Fluid within the Skin," by Levinson, et al., published as U.S. Pat. Apl. Pub. No. 2011/0009847 on Jan. 13, 2011; U.S. patent application Ser. No. 12/716,226, filed Mar. 2, 2010, entitled "Techniques and Devices Associated with Blood Sampling," by Levinson, et al., published as U.S. Pat. Apl. Pub. No. 2010/0256524 on Oct. 7, 2010; U.S. patent application Ser. No. 12/716,229, filed Mar. 2, 2010, entitled "Devices and Techniques Associated with Diagnostics, Therapies, and Other Applications, Including Skin-Associated Applications," by Bernstein, et al., published as U.S. Pat. Apl. Pub. No. 2010/0256465 on Oct. 7, 2010; U.S. patent application Ser. No. 12/953,744, filed Nov. 24, 2010, entitled "Patient-Enacted Sampling Technique," by Levinson, et al.; U.S. patent application Ser. No. 12/915,735, filed Oct. 29, 2010, entitled "Systems and Methods for Application to Skin and Control of Actuation, Delivery, and/or Perception Thereof," by Chickering, et al.; U.S. patent application Ser. No. 12/915,789, filed Oct. 29, 2010, entitled "Systems and Methods for Treating, Sanitizing, and/or Shielding the Skin or Devices Applied to the Skin," by Bernstein, et al.; U.S. patent application Ser. No. 12/915,820, filed Oct. 29, 2010, entitled "Relatively Small Devices Applied to the Skin, Modular Systems, and Methods of Use Thereof," by Bernstein, et al.; U.S. patent application Ser. No. 13/006,177, filed Jan. 13, 2011, entitled "Rapid Delivery and/or Withdrawal of Fluids," by Chickering, et al.; U.S. patent application Ser. No. 13/006,165, filed Jan. 13, 2011, entitled "Sampling Device Interfaces," by Chickering, et al.; U.S. Prov. Pat. Apl. Ser. No. 61/357,582, filed Jun. 23, 2010, entitled "Sampling Devices and Methods Involving Relatively Little Pain," by Chickering, et al.; U.S. Prov. Pat. Apl. Ser. No. 61/367,607, filed Jul. 26, 2010, entitled "Rapid Delivery and/or Withdrawal of Fluids," by Davis, et al.; U.S. Prov. Pat. Apl. Ser. No. 61/373,764, filed Aug. 13, 2010, entitled "Clinical and/or Consumer Techniques and Devices," by Chickering, et al.; and U.S. Prov. Pat. Apl. Ser. No. 61/411,566, filed Nov. 9, 2010, entitled "Systems and Interfaces for Blood Sampling," by Brancazio, et al.

Also incorporated herein by reference in their entireties are U.S. Provisional Patent Application Ser. No. 61/480,977, entitled "Delivering and/or Receiving Fluids," by Gonzales-Zugasti, et al., and U.S. Provisional Patent Application Ser. No. 61/480,960, entitled "Methods and Devices for Withdrawing Fluids from a Subject Using Reduced Pressure," by Haghgooie, et al., each filed on Apr. 29, 2011. Also incorporated herein by reference in their entireties are U.S. and international patent applications each entitled "Delivering and/or Receiving Fluids," and U.S. and international patent applications each entitled "Methods and Devices for Withdrawing Fluids from a Subject Using Reduced Pressure," each of which is filed on even date herewith. In addition, U.S. Provisional Patent Application Ser. No. 61/480,941, filed Apr. 29, 2011, entitled "Plasma or Serum Production and Removal of Fluids under Reduced Pressure," by Haghgooie, et al., and U.S. Provisional Patent Application Ser. No. 61/549,437, filed Oct. 20, 2011, entitled "Systems and Methods for Collection and/or Manipulation of Blood Spots or Other Bodily Fluids," by Bernstein, et al. are each incorporated herein by reference in its entirety.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for receiving bodily fluid from a subject and processing the bodily fluid to form plasma or serum, the device comprising:
    an opening for introduction of a bodily fluid from the subject into the device;
    a separation membrane in fluid communication with the opening on a first side of the membrane, the separation membrane sized such that the bodily fluid passing therethrough is separated to form plasma or serum;
    a vacuum chamber having a pressure less than ambient pressure before the device is applied to the skin of the subject;
    a seal that can be manipulated to control a fluid communication pathway between the vacuum chamber and a second side of the separation membrane; and
    a flow activator comprising one or more microneedles positioned to cause release of bodily fluid from the subject.

2. The device of claim 1, wherein the separation membrane comprises a polysulfone.

3. The device of claim 1, wherein the separation membrane comprises a polyethersulfone.

4. The device of claim 1, wherein the separation membrane comprises a nitrocellulose.

5. The device of claim 1, wherein the separation membrane has an average pore diameter of less than about 20 micrometers.

6. The device of claim 1, wherein the separation membrane has an average pore diameter of less than about 8 micrometers.

7. The device of claim 1, wherein the separation membrane has an average pore diameter of less than about 4 micrometers.

8. The device of claim 1, wherein the opening is positioned within an applicator region positioned to collect bodily fluid from the skin of the subject.

9. The device of claim 1, wherein the vacuum chamber has a pressure, prior to introduction of a bodily fluid from the subject into the device, that is lower than about 100 mmHg below ambient pressure.

10. The device of claim 1, further comprising a storage chamber in fluid communication with the second side of the separation membrane.

11. The device of claim 10, wherein the storage chamber contains an anticoagulant.

12. The device of claim 1, wherein the separation membrane has an area less than 5 square centimeters.

13. The device of claim 1, wherein the separation membrane has an area less than 1 square centimeter.

14. The device of claim 1, wherein the separation membrane has an area less than 0.5 square centimeters.

15. The device of claim 1, wherein the separation membrane contains an anticoagulant.

16. The device of claim 1, wherein the fluid communication pathway contains an anticoagulant.

* * * * *